United States Patent
Hashimoto

(10) Patent No.: US 11,715,279 B2
(45) Date of Patent: Aug. 1, 2023

(54) WEIGHTED IMAGE GENERATION APPARATUS, METHOD, AND PROGRAM, DETERMINER LEARNING APPARATUS, METHOD, AND PROGRAM, REGION EXTRACTION APPARATUS, METHOD, AND PROGRAM, AND DETERMINER

(71) Applicant: FUJIFILM Corporation, Tokyo (JP)

(72) Inventor: Takayuki Hashimoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 300 days.

(21) Appl. No.: 17/237,076

(22) Filed: Apr. 22, 2021

(65) Prior Publication Data
US 2021/0241016 A1 Aug. 5, 2021

Related U.S. Application Data

(63) Continuation of application No. PCT/JP2019/041401, filed on Oct. 21, 2019.

(30) Foreign Application Priority Data
Oct. 25, 2018 (JP) .................... 2018-201071

(51) Int. Cl.
*G06V 10/25* (2022.01)
*G06F 18/21* (2023.01)

(52) U.S. Cl.
CPC ........... *G06V 10/25* (2022.01); *G06F 18/217* (2023.01); *G06V 2201/03* (2022.01)

(58) Field of Classification Search
CPC .. G06V 10/25; G06V 2201/03; G06F 18/217; A61B 5/055; A61B 6/03; G01T 1/161; G06T 7/00; G06T 7/136
See application file for complete search history.

(56) References Cited

U.S. PATENT DOCUMENTS

| 8,081,811 B2 | 12/2011 | Moriya | |
| 2010/0111394 A1* | 5/2010 | Okamura | G06T 7/13 382/199 |
| 2017/0301093 A1* | 10/2017 | Nakagomi | G06T 5/50 |

FOREIGN PATENT DOCUMENTS

| JP | 11128226 | 5/1999 |
| JP | 2002210027 | 7/2002 |

(Continued)

OTHER PUBLICATIONS

Leng et al., "Correlation between model observer and human observer performance in CT imaging when lesion location is uncertain", Med. Phys. 40 (8), Aug. 2013 (Year: 2013).*

(Continued)

*Primary Examiner* — Qian Yang
(74) *Attorney, Agent, or Firm* — JCIPRNET

(57) ABSTRACT

A display control unit displays a medical image from which at least one region of interest is extracted on a display unit. A correction unit corrects a boundary of the region of interest according to a correction instruction for the boundary of the region of interest extracted from the displayed medical image. An image generation unit generates a weighted image in which each pixel in the medical image has, as a pixel value of each pixel, a weight coefficient representing a weight of being within the region of interest, by setting an initial weight coefficient for the extracted region of interest and setting a corrected weight coefficient for a corrected region for which the correction instruction is given in the medical image.

20 Claims, 15 Drawing Sheets

(56) References Cited

FOREIGN PATENT DOCUMENTS

JP          2009095644          5/2009
WO          2008107970          9/2008

OTHER PUBLICATIONS

Yan et al., "Semiautomatic segmentation of liver metastases on volumetric CT images", Med. Phys. 42 (11 ), Nov. 2015 (Year: 2015).*
Balagurunathan et al., "Reproducibility and Prognosis of Quantitative Features Extracted from CT Images", Translational Oncology vol. 7. No. 1, 2014 (Year: 2014).*
Machine Translation for JP2002-210027, IDS (Year: 2002).*
"International Search Report (Form PCT/ISA/210) of PCT/JP2019/041401," dated Dec. 24, 2019, with English translation thereof, pp. 1-5.
"Written Opinion of the International Searching Authority (Form PCT/ISA/237) of PCT/JP2019/041401," dated Dec. 24, 2019, with English translation thereof, pp. 1-7.

* cited by examiner

WEIGHTED IMAGE GENERATION APPARATUS, METHOD, AND PROGRAM, DETERMINER LEARNING APPARATUS, METHOD, AND PROGRAM, REGION EXTRACTION APPARATUS, METHOD, AND PROGRAM, AND DETERMINER

CROSS REFERENCE TO RELATED APPLICATIONS

The present application is a Continuation of PCT International Application No. PCT/JP2019/041401 filed on Oct. 21, 2019, which claims priority under 35 U.S.C. § 119(a) to Japanese Patent Application No. 2018-201071 filed on Oct. 25, 2018. Each of the above applications is hereby expressly incorporated by reference, in its entirety, into the present application.

BACKGROUND

Technical Field

The present disclosure relates to a weighted image generation apparatus, a weighted image generation method, and a weighted image generation program that generate a weighted image representing a weight for a region of interest included in a medical image; a determiner learning apparatus, a determiner learning method, a determiner learning program; a region extraction apparatus, a region extraction method, a region extraction program; and a determiner.

Related Art

In recent years, with advancements in medical apparatuses such as a computed tomography (CT) apparatus and a magnetic resonance imaging (MRI) apparatus, image diagnosis using higher quality and higher resolution three-dimensional medical images has become possible. A region of interest such as an organ and a lesion included in a three-dimensional medical image is also automatically extracted using a determiner that is learned using an artificial intelligence (AI) technology. However, in a case where the region of interest is automatically extracted, over-extraction and insufficient extraction may occur. In such a case, it is necessary to correct a boundary of the region of interest which is automatically extracted.

A method of automatically correcting the boundary of the region of interest extracted in this way has been proposed (refer to JP2009-095644A). On the other hand, there is a case where a determiner capable of performing more advanced extraction is learned by using, as learning data, the region of interest automatically extracted by an existing determiner. In such a case, in order to improve learning accuracy, it is necessary to correct the boundary of the region of interest extracted by the existing determiner and to use the corrected region of interest as learning data with higher accuracy. However, even in a case where the boundary of the region of interest is corrected by using the method described in JP2009-095644A, it is difficult to accurately set the boundary of the region of interest. For this reason, practically, in many cases, a medical image from which the region of interest is extracted is displayed, and correction of the boundary of the region of interest is performed by a manual operation by a user. In a case where the boundary of the region of interest is corrected by a manual operation, the medical image is displayed, and by dragging a circular cursor in the displayed medical image, an over-extracted region is deleted, or a region is added to the region of interest with insufficient extraction. Thereby, the boundary is edited.

However, in a case where the boundary of the region of interest as an extraction target is unclear, the intended boundary of the region of interest may differ depending on the user who performs the correction. In addition, even for the same user, the boundary of the region of interest may be changed depending on an editing timing. Further, during a work of correcting the boundary, a threshold value of the image for defining the boundary may be changed. For this reason, in a case where the boundary of the region of interest is unclear, the boundary of the region of interest is set by repeatedly performing region addition and region deletion at the boundary. On the other hand, in a case where the determiner is learned by using, as learning data, the region of interest of which the boundary is set in this way, the boundary of the region of interest extracted by the determiner tends to be unstable. As a result, in a case where the determiner learned in this way is used, the region of interest may be erroneously detected.

SUMMARY OF THE INVENTION

The present invention has been made in view of the above circumstances, and an object of the present invention is to make it possible to set a region in a medical image by reflecting correction of a boundary.

According to the present disclosure, there is provided a weighted image generation apparatus including: a display control unit that displays a medical image from which at least one region of interest is extracted on a display unit; a correction unit that corrects a boundary of the region of interest according to a correction instruction for the extracted region of interest; and an image generation unit that generates a weighted image in which each pixel in the medical image has, as a pixel value of each pixel, a weight coefficient representing a certainty of being within the region of interest, by setting an initial weight coefficient for the extracted region of interest and setting a corrected weight coefficient for a corrected region based on the correction instruction in the medical image.

In the weighted image generation apparatus according to the present disclosure, the image generation unit may set at least one of corrected weight coefficients having different values according to content of the correction instruction.

Further, in the weighted image generation apparatus according to the present disclosure, the image generation unit may set a corrected weight coefficient having a positive value for the corrected region in a case where the correction instruction is a region addition instruction, and may set a corrected weight coefficient having a negative value for the corrected region in a case where the correction instruction is a region deletion instruction.

Further, in the weighted image generation apparatus according to the present disclosure, in a case where a plurality of regions of interest are extracted from the medical image, the correction unit may correct a boundary of each of the plurality of regions of interest according to the correction instruction for each of the plurality of regions of interest, and the image generation unit may set the weight coefficients for each of the plurality of regions of interest.

Further, in the weighted image generation apparatus according to the present disclosure, the image generation unit may set boundaries of the plurality of regions of interest according to a threshold value which is set for the weight coefficient of at least one region of interest among the plurality of regions of interest.

Further, in the weighted image generation apparatus according to the present disclosure, in a case where the plurality of regions of interest are adjacent to each other, the image generation unit may set boundaries of the plurality of regions of interest in the weighted image according to the weight coefficients which are set for each of the plurality of regions of interest.

Further, in the weighted image generation apparatus according to the present disclosure, the image generation unit may set, according to the correction instruction for one region of interest among the plurality of regions of interest, the corrected weight coefficients for other region of interests other than the one region of interest.

Further, in the weighted image generation apparatus according to the present disclosure, the image generation unit may set at least one of corrected weight coefficients having different values according to a type of the region of interest.

Further, in the weighted image generation apparatus according to the present disclosure, in a case where the medical image is a three-dimensional image, the image generation unit may set, in the medical image displayed on the display unit, the corrected weight coefficient for a visually recognizable pixel to be larger than the corrected weight coefficient for a visually unrecognizable pixel.

Further, the weighted image generation apparatus according to the present disclosure may further include a threshold value setting unit that sets a threshold value for the weight coefficient, and a corresponding region extraction unit that extracts, from the medical image, a corresponding region corresponding to a region for which the weight coefficient is equal to or larger than the threshold value in the weighted image.

According to the present disclosure, there is provided a determiner learning apparatus including: a learning data acquisition unit that acquires, as learning data, the weighted image generated by the weighted image generation apparatus according to the present disclosure and an image of the corresponding region extracted from the medical image; and a learning unit that learns a determiner, which outputs a determination result of a region of interest included in the medical image in a case where the medical image is input, using a plurality of pieces of the learning data.

According to the present disclosure, there is provided a determiner learned by the determiner learning apparatus according to the present disclosure.

According to the present disclosure, there is provided a region extraction apparatus including: an image acquisition unit that acquires a medical image including a region of interest as a determination target; and the determiner according to the present disclosure that determines the region of interest in the medical image.

The region extraction apparatus according to the present disclosure may further include a display control unit that displays a determination result of the region of interest by the determiner.

According to the present disclosure, there is provided a weighted image generation method including: displaying a medical image from which at least one region of interest is extracted on a display unit; correcting a boundary of the region of interest according to a correction instruction for the extracted region of interest; and generating a weighted image in which each pixel in the medical image has, as a pixel value of each pixel, a weight coefficient representing a certainty of being within the region of interest, by setting an initial weight coefficient for the extracted region of interest and setting a corrected weight coefficient for a corrected region based on the correction instruction in the medical image.

According to the present disclosure, there is provided a determiner learning method including: acquiring, as learning data, the weighted image generated by the weighted image generation method according to the present disclosure and an image of a corresponding region extracted from the medical image and corresponding to a region for which the weight coefficient is equal to or larger than a threshold value in the weighted image; and learning a determiner, which outputs a determination result of a region of interest included in the medical image in a case where the medical image is input, using a plurality of pieces of the learning data.

According to the present disclosure, there is provided a region extraction method including: acquiring a medical image including a region of interest as a determination target; and determining the region of interest in the medical image by the determiner according to the present disclosure.

The weighted image generation method, the determiner learning method, and the region extraction method according to the present disclosure may be provided as a program for causing a computer to execute the method.

According to the present disclosure, there is further provided a weighted image generation apparatus including: a memory that stores an instruction to be executed by a computer; and a processor configured to execute the stored instruction, in which the processor is configured to execute processing of displaying a medical image from which at least one region of interest is extracted on a display unit, correcting a boundary of the region of interest according to a correction instruction for the extracted region of interest, and generating a weighted image in which each pixel in the medical image has, as a pixel value of each pixel, a weight coefficient representing a certainty of being within the region of interest, by setting an initial weight coefficient for the extracted region of interest and setting a corrected weight coefficient for a corrected region based on the correction instruction in the medical image.

According to the present disclosure, there is further provided a determiner learning apparatus including: a memory that stores an instruction to be executed by a computer; and a processor configured to execute the stored instruction, in which the processor is configured to execute processing of acquiring, as learning data, the weighted image generated by the weighted image generation method according to the present disclosure and an image of the corresponding region extracted from the medical image, and learning a determiner, which outputs a determination result of a region of interest included in the medical image in a case where the medical image is input, using a plurality of pieces of the learning data.

According to the present disclosure, there is further provided a region extraction apparatus including: a memory that stores an instruction to be executed by a computer; and a processor configured to execute the stored instruction, in which the processor is configured to execute processing of acquiring a medical image including a region of interest as a determination target, and determining the region of interest in the medical image by the determiner according to the present disclosure.

According to the present disclosure, it is possible to set the region of interest in the medical image by appropriately reflecting correction of the boundary.

DETAILED DESCRIPTION

Figure 1:
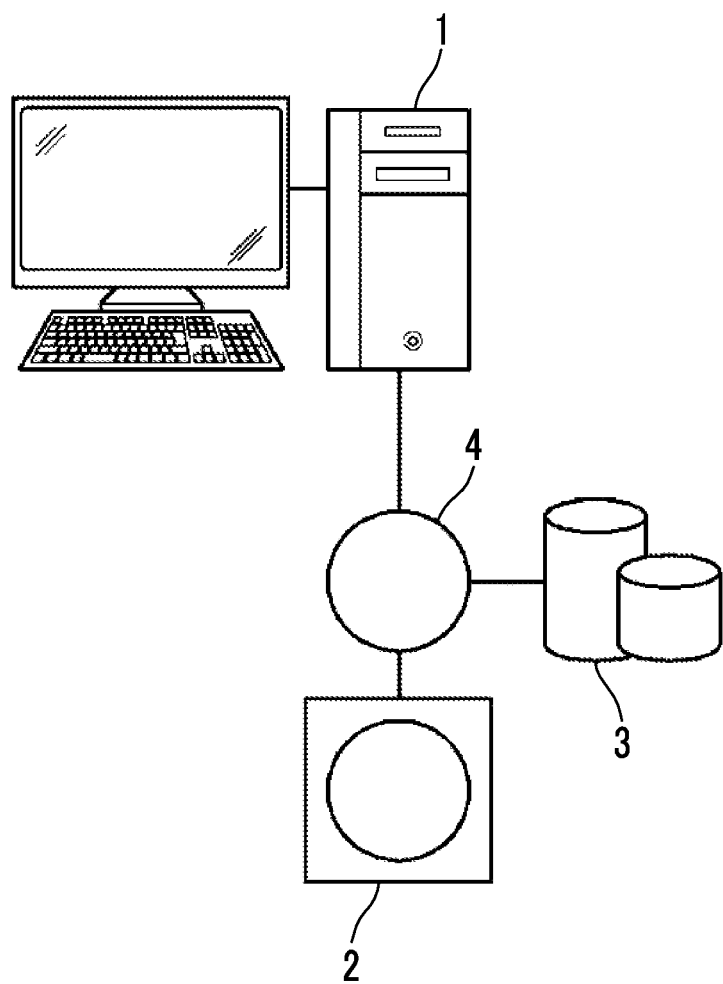
FIG. 1 is a hardware configuration diagram illustrating an outline of a diagnosis support system to which a weighted image generation apparatus according to an embodiment of the present disclosure is applied.

Hereinafter, embodiments of the present disclosure will be described with reference to the drawings. FIG. 1 is a hardware configuration diagram illustrating an outline of a diagnosis support system to which a weighted image generation apparatus according to an embodiment of the present disclosure is applied. As illustrated in FIG. 1, in the diagnosis support system, a weighted image generation apparatus 1, a three-dimensional image capturing apparatus 2, and an image storage server 3 according to the present embodiment are connected to communicate with each other via a network 4.

The three-dimensional image capturing apparatus 2 is an apparatus that generates a three-dimensional image representing a region of a subject as a diagnosis target by capturing the region, and is, specifically, a CT apparatus, an MRI apparatus, a positron emission tomography (PET) apparatus, or the like. The three-dimensional image generated by the three-dimensional image capturing apparatus 2 is transmitted to the image storage server 3 and is stored. In the present embodiment, the three-dimensional image capturing apparatus 2 is a CT apparatus, and a CT image including a region of a subject as a diagnosis target is generated as a three-dimensional image G0. Further, the three-dimensional image G0 includes a plurality of tomographic images. The three-dimensional image G0 and the plurality of tomographic images included in the three-dimensional image G0 correspond to medical images according to the present disclosure.

The image storage server 3 is a computer that stores and manages various data, and includes a large-capacity external storage device and database management software. The image storage server 3 communicates with another apparatus via a wired or wireless network 4 to transmit and receive image data and the like. Specifically, the image storage server 3 acquires various data including the image data of the three-dimensional image G0 generated by the three-dimensional image capturing apparatus 2 via the network, and stores and manages the acquired data in a recording medium such as a large-capacity external storage device. A storage format of the image data and a communication between the apparatuses via the network 4 are based on a protocol such as digital imaging and communication in medicine (DICOM).

The weighted image generation apparatus 1 is a computer in which the weighted image generation program according to the present embodiment is installed. The computer may be a workstation or a personal computer directly operated by a doctor who performs diagnosis, or may be a server computer connected to the workstation or the personal computer via a network. The weighted image generation program is distributed by being recorded on a recording medium such as a digital versatile disc (DVD) or a compact disc read only memory (CD-ROM), and is installed in a computer from the recording medium. Alternatively, the weighted image generation program is stored in a storage device of a server computer or in a network storage connected to the network to be accessible from the outside, and is downloaded and installed in the computer used by the doctor according to a request.

Figure 2:
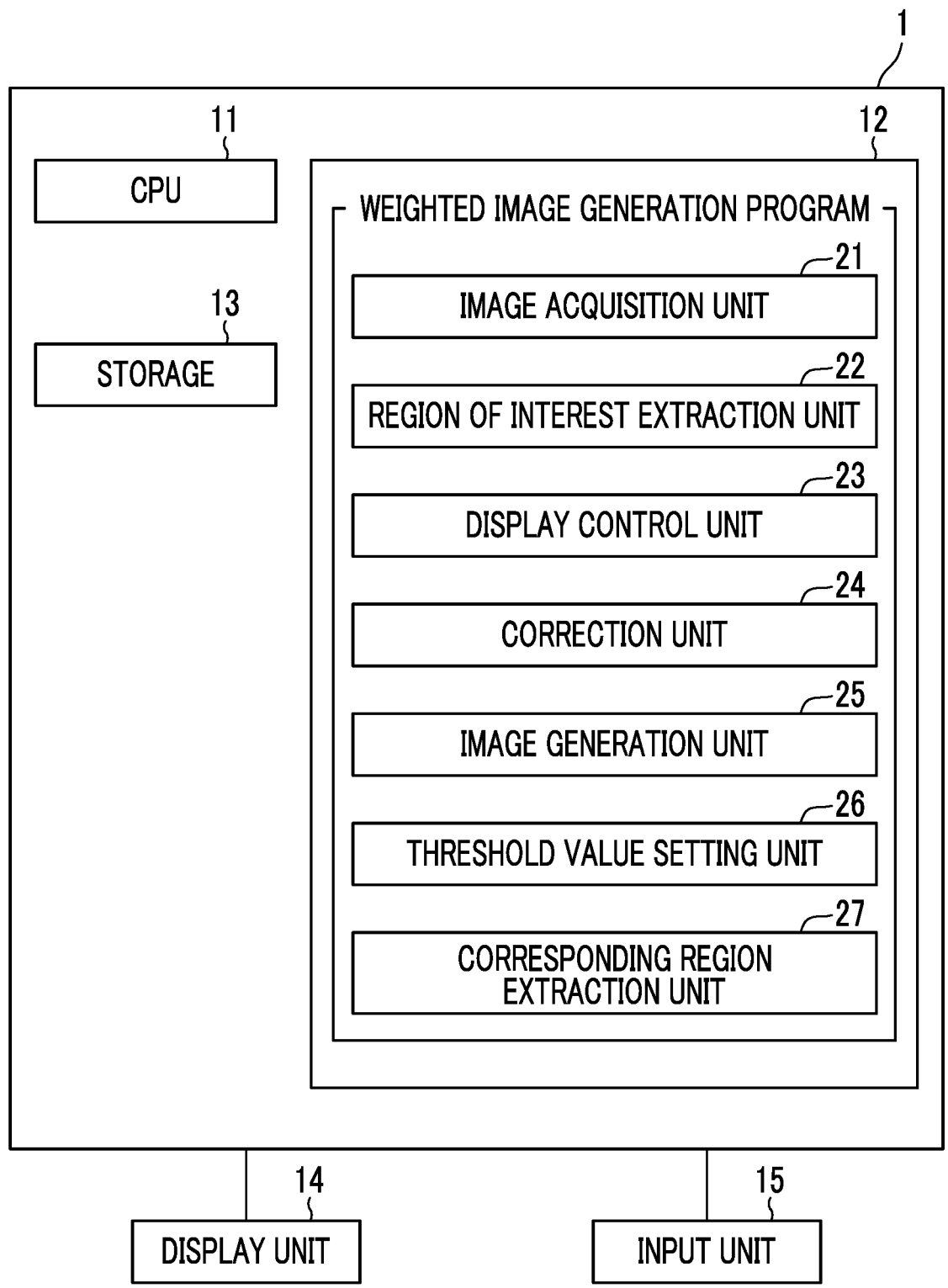
FIG. 2 is a diagram illustrating a schematic configuration of the weighted image generation apparatus according to the embodiment of the present disclosure.

FIG. 2 is a diagram illustrating a schematic configuration of the weighted image generation apparatus according to the present embodiment, which is realized by installing the weighted image generation program in a computer. As illustrated in FIG. 2, the weighted image generation apparatus 1 includes a central processing unit (CPU) 11, a memory 12, and a storage 13 as a standard workstation configuration. Further, a display unit 14 such as a liquid crystal display, and an input unit 15 such as a keyboard and a mouse are connected to the weighted image generation apparatus 1.

The storage 13 includes a hard disk drive or the like, and stores various information including the three-dimensional image G0 acquired from the image storage server 3 via the network 4 and information required for processing.

Further, the weighted image generation program is stored in the memory 12. The weighted image generation program defines, as processing to be executed by the CPU 11, image acquisition processing of acquiring a three-dimensional image G0, region of interest extraction processing of extracting a region of interest from the three-dimensional image G0, display control processing of displaying the three-dimensional image G0 on a display unit 14, correction processing of correcting a boundary of the region of interest according to a correction instruction for the boundary of the region of interest extracted from the displayed three-dimensional image G0, image generation processing of generating a weighted image in which each pixel in the three-dimensional image G0 has, as a pixel value of each pixel, a weight coefficient representing a certainty of being within the region of interest, by setting an initial weight coefficient for the extracted region of interest and setting a corrected weight coefficient for a corrected region for which a correction instruction is given in the three-dimensional image G0, threshold value setting processing of setting a threshold value for the weight coefficient, and corresponding region extraction processing of extracting, from the three-dimensional image G0, a corresponding region corresponding to a region including pixels of which the weight coefficient is equal to or larger than the threshold value in the weighted image.

In a case where the CPU 11 executes the processing according to the program, the computer functions as an image acquisition unit 21, a region of interest extraction unit 22, a display control unit 23, a correction unit 24, an image generation unit 25, a threshold value setting unit 26, and a corresponding region extraction unit 27.

The image acquisition unit 21 acquires the three-dimensional image G0 including the region of interest from the image storage server 3. The region of interest is a region of a structure such as an organ, a lesion, a bone, and a cartilage that the user is interested in, as a diagnosis target. In a case where the three-dimensional image G0 is already stored in the storage 13, the image acquisition unit 21 may acquire the three-dimensional image G0 from the storage 13.

The region of interest extraction unit 22 extracts a region of interest from the three-dimensional image G0. For extraction of a region of interest, the region of interest extraction unit 22 includes a learned model obtained by performing machine learning so as to extract the region of interest from the three-dimensional image G0. The learned model includes a neural network obtained by performing deep learning so as to extract, as a region of interest, an structure such as an organ, a lesion, a bone, and a cartilage as a diagnosis target. In a case where the three-dimensional image G0 is input, the learned model outputs a determination result representing whether or not each pixel of the three-dimensional image G0 is within a region of interest. The region of interest extraction unit 22 extracts, as a region of interest, a region including pixels determined to be within a region of interest.

In addition to the neural network obtained by performing deep learning, the learned model may include, for example, a support vector machine (SVM), a convolutional neural network (CNN), a recurrent neural network (RNN), and the like. Further, the region of interest extraction unit 22 is not limited to a unit including the learned model obtained by performing machine learning. For example, the region of interest may be extracted by template matching or the like.

Figure 3:
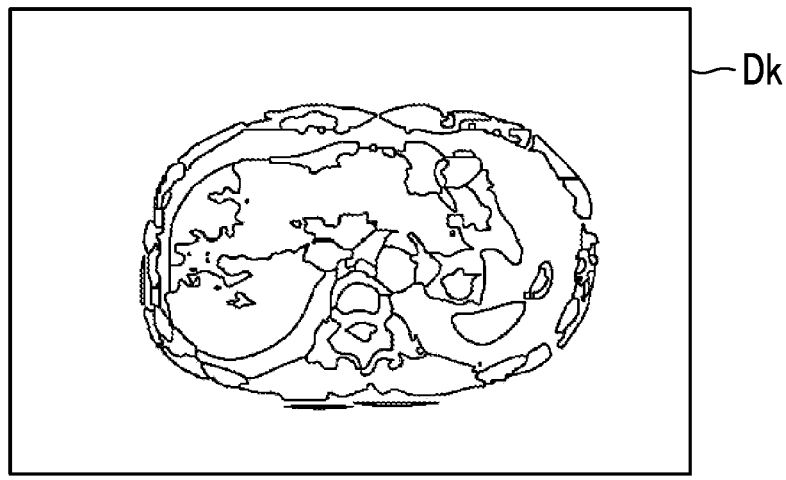
FIG. 3 is a diagram illustrating a tomographic image displayed on a display unit.

The display control unit 23 displays the three-dimensional image G0 on the display unit 14. In the present embodiment, a plurality of tomographic images Dj (j is a number from 1 to n, n is the number of tomographic images) included in the three-dimensional image G0 are sequentially displayed according to an instruction from the input unit 15. In the present embodiment, the user corrects a boundary of the region of interest in the tomographic image Dj sequentially displayed. FIG. 3 is a diagram illustrating a tomographic image displayed on the display unit 14. The displayed tomographic image may be a tomographic image having any cross section of an axial cross section, a sagittal cross section, and a coronal cross section. In the present embodiment, as illustrated in FIG. 3, for example, it is assumed that one abdomen tomographic image Dk having an axial section is displayed.

Figure 4:
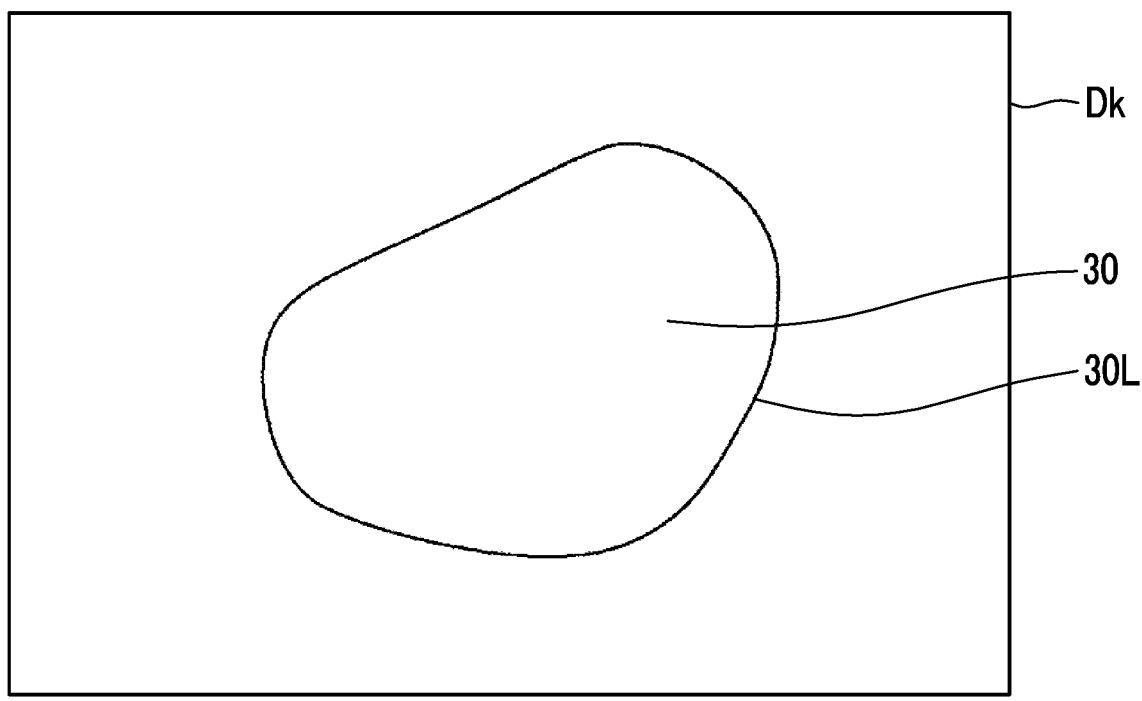
FIG. 4 is a diagram for explaining correction of a boundary of a region of interest.

The correction unit 24 corrects the boundary of the region of interest in the tomographic image Dk displayed on the display unit 14 according to a correction instruction by the user. FIG. 4 is a diagram for explaining the correction of the boundary of the region of interest. In FIG. 4, for the sake of explanation, the region of interest is enlarged and displayed. As illustrated in FIG. 4, the tomographic image Dk includes the boundary 30L of the extracted region of interest 30. The region of interest 30 is included in the tomographic image Dk, as a mask. The mask may be one representing only an outline of the region of interest 30, may be one hatched within the region, or may be one filled with a predetermined color within the region. In the following description, it is assumed that the region of interest 30 means a masked region in the tomographic image Dk. Here, the extraction result of the region of interest 30 by the region of interest extraction unit 22 is not always accurate, and the region of interest 30 may not match with the actual region of interest included in the tomographic image Dk. For example, the region of interest 30 that is larger than the actual region of interest may be extracted by over-extraction. On the contrary, due to insufficient extraction, the region of interest 30 that is smaller than the actual region of interest may be extracted.

In such a case, the user corrects the boundary 30L of the extracted region of interest 30 by using the input unit 15. Specifically, in a case where a correction instruction is input from the input unit 15, a circular cursor 40 is displayed on the display unit 14 by the correction unit 24. The user performs a correction instruction by moving the cursor 40 using the mouse of the input unit 15 such that the boundary 30L of the region of interest 30 matches with the boundary of the actual region of interest. The correction unit 24 corrects the boundary 30L of the region of interest 30 according to the correction instruction by the user. The shape of the cursor 40 is not limited to a circle, and may be any shape such as a rectangular shape, a triangular shape, and an arrow shape.

Figure 5:
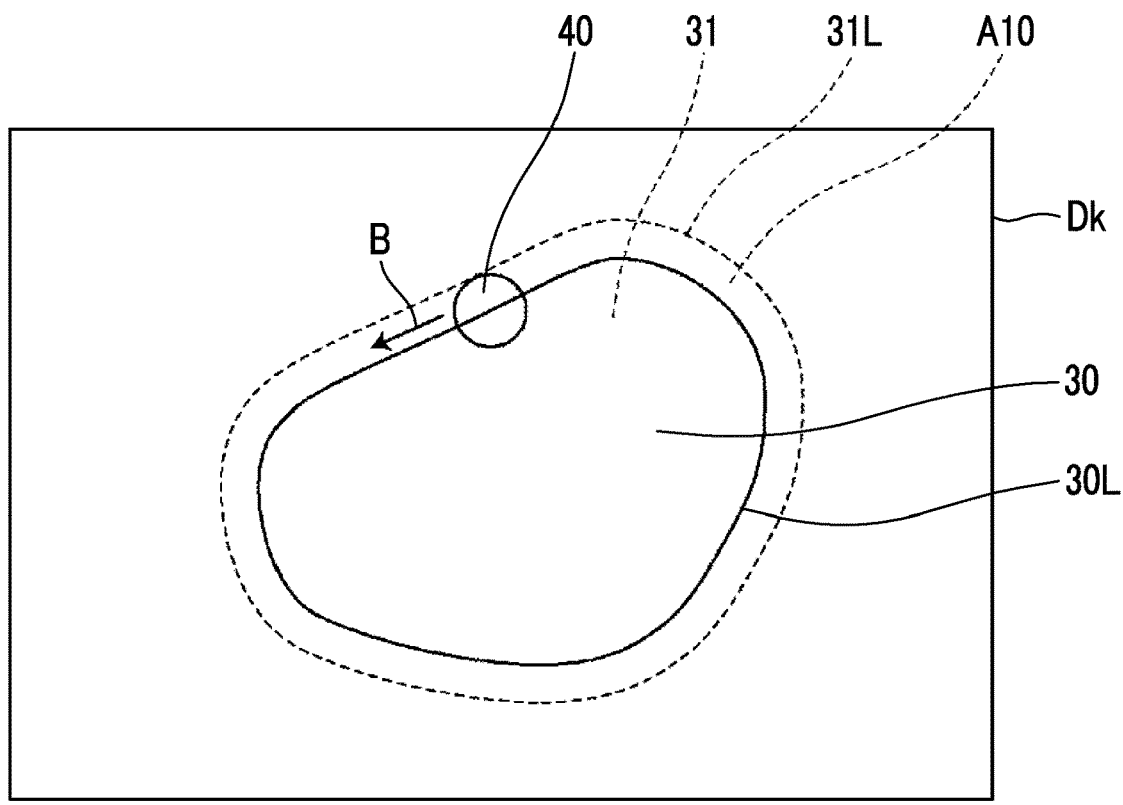
FIG. 5 is a diagram for explaining correction of the boundary of the region of interest in a case of insufficient extraction.

FIG. 5 is a diagram for explaining the correction of the boundary of the region of interest in a case of insufficient extraction. As illustrated in FIG. 5, for a region A10 in which the extraction of the region of interest 30 is insufficient with respect to the actual region of interest 31, while the user performs a region addition instruction, the user performs an instruction to add the insufficient region A10 to the region of interest 30 by moving an outer edge of the cursor 40 along the boundary 31L of the actual region of interest 31, for example, in a direction of an arrow B. The region addition instruction may be, for example, a left click of the mouse included in the input unit 15 or a predetermined combination of pressing of a cursor and a click of the mouse, and is not limited thereto.

Figure 6:
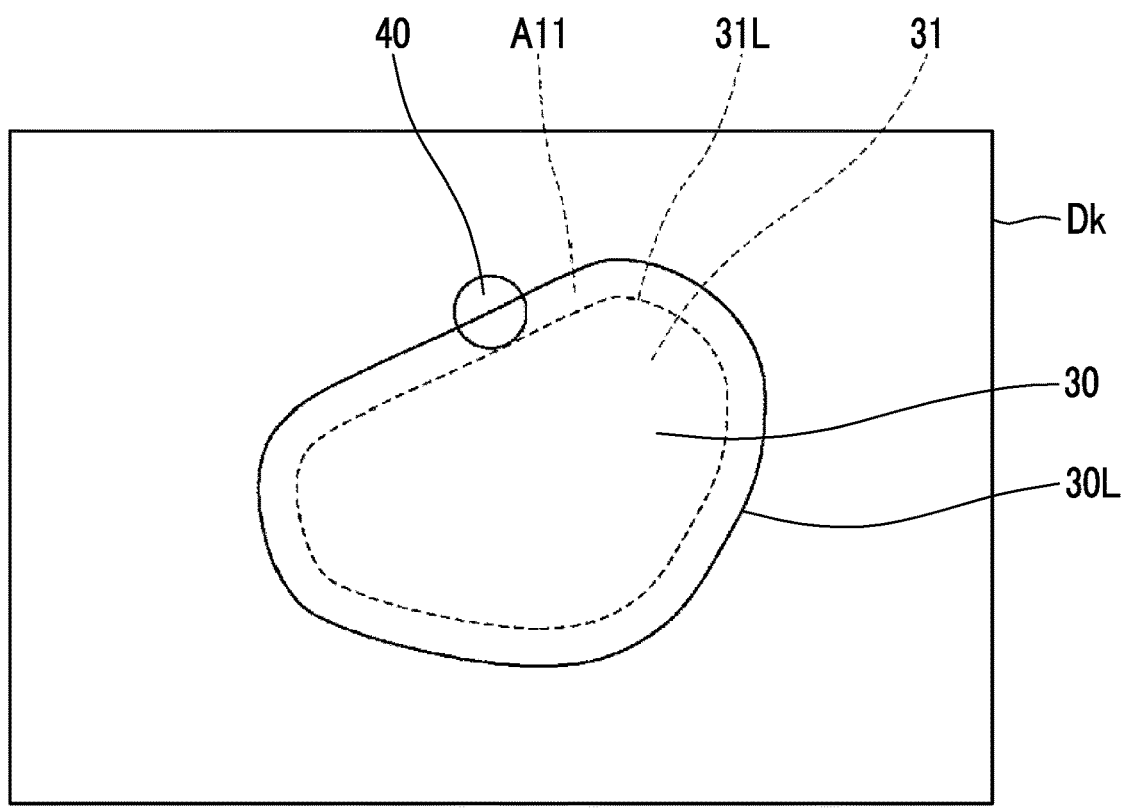
FIG. 6 is a diagram for explaining correction of the boundary of the region of interest in a case of over-extraction.

FIG. 6 is a diagram for explaining the correction of the boundary of the region of interest in a case of over-extraction. As illustrated in FIG. 6, for a region A11 in which the first region of interest 30 is over-extracted with respect to the actual region of interest 31, while the user performs a region deletion instruction, the user performs an instruction to delete the over-extracted region A11 from the region of interest 30 by moving an outer edge of the cursor 40 along the boundary 31L of the actual region of interest 31. The region deletion instruction may be, for example, a right click of the mouse included in the input unit 15 or a predetermined combination of pressing of a cursor and a click of the mouse, and is not limited thereto.

The image generation unit 25 sets an initial weight coefficient for the extracted region of interest, and sets a corrected weight coefficient for the corrected region for which the correction instruction is given in the three-dimensional image G0, that is, in the tomographic image Dk. Thereby, the image generation unit 25 generates a weighted image W0 in which each pixel has, as a pixel value of each pixel, the weight coefficient representing the certainty of being within the region of interest. Each pixel of the weighted image W0 corresponds to each pixel of the three-dimensional image G0. In the present embodiment, for example, the initial weight coefficient is set to 100, the corrected weight coefficient which is set for the region added by the correction is set to +4, and the corrected weight coefficient which is set for the region deleted by the correction is set to −4. The values of the initial weight coefficient and the corrected weight coefficient are not limited to these values. For example, a negative value may be set as the initial weight coefficient. Further, for example, a corrected weight coefficient having a negative value may be set for the added region, and a corrected weight coefficient having a positive value may be set for the deleted region. Further, the corrected weight coefficient may be set to a positive value, and the corrected weight coefficient for the added region may have a value larger than a value of the corrected weight coefficient for the deleted region.

Figure 7:
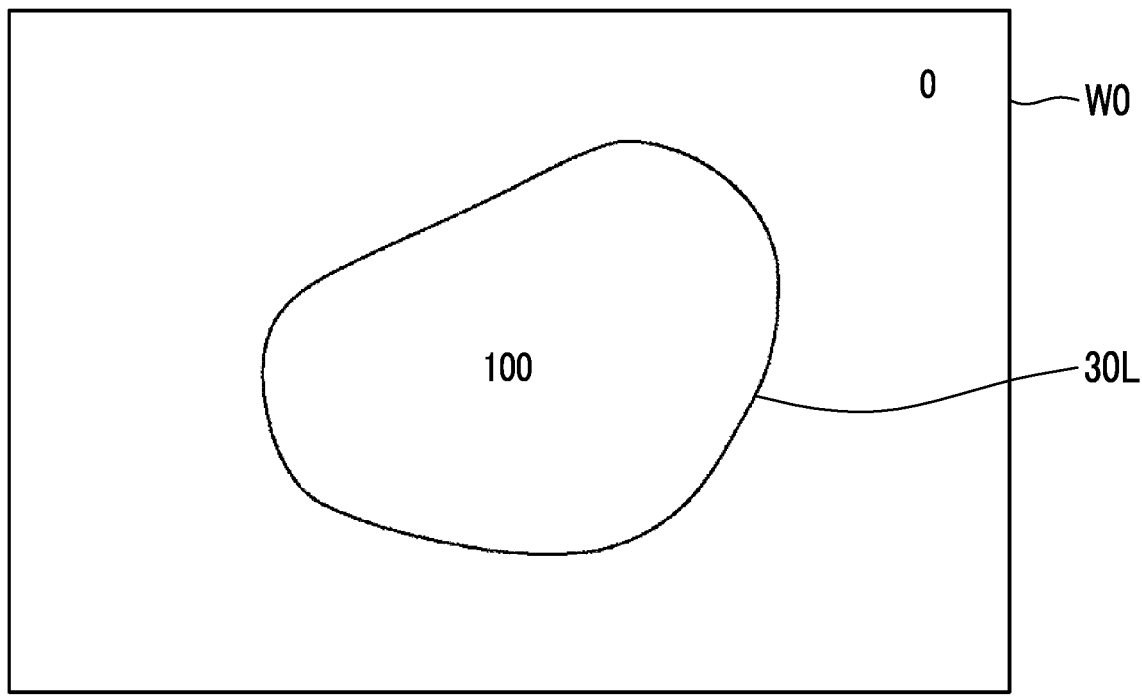
FIG. 7 is a diagram illustrating a weighted image in which only an initial weight coefficient is set.

FIG. 7 is a diagram illustrating a weighted image W0 in which only the initial weight coefficient is set. As illustrated in FIG. 7, in the weighted image W0, the weight coefficient of the region corresponding to the region of interest 30 surrounded by the boundary 30L is 100, and the weight coefficient of the other regions is 0.

Figure 8:
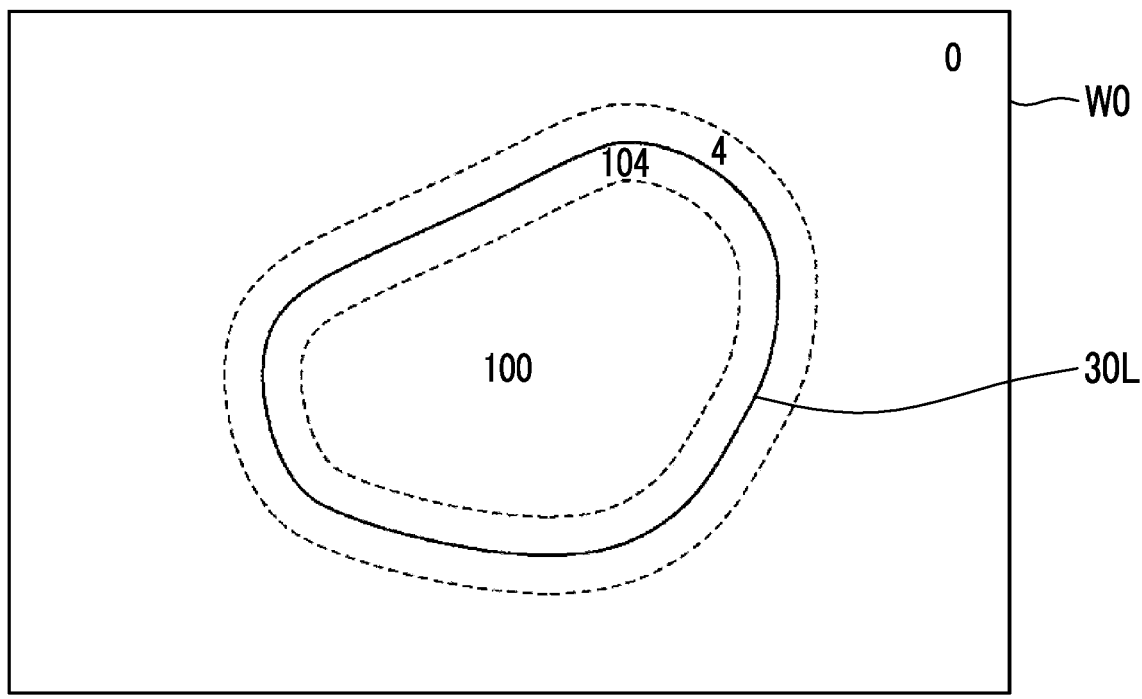
FIG. 8 is a diagram illustrating a weighted image after the weight coefficient is corrected.

On the other hand, in the weighted image W0 illustrated in FIG. 7, in a case where correction for adding the region A10 is performed as illustrated in FIG. 5, a corrected weight coefficient of +4 is set for the region through which the cursor 40 passes. That is, the corrected weight coefficient of +4 is set for a portion through which the cursor 40 passes inside the boundary 30L of the region of interest 30, and thus the weight coefficient of the portion is 104. Further, the corrected weight coefficient of +4 is set for a portion through which the cursor 40 passes outside the boundary 30L of the region of interest 30, and thus the weight coefficient of the portion is 4. Thereby, the weight coefficients in the weighted image W0 are as illustrated in FIG. 8.

Figure 9:
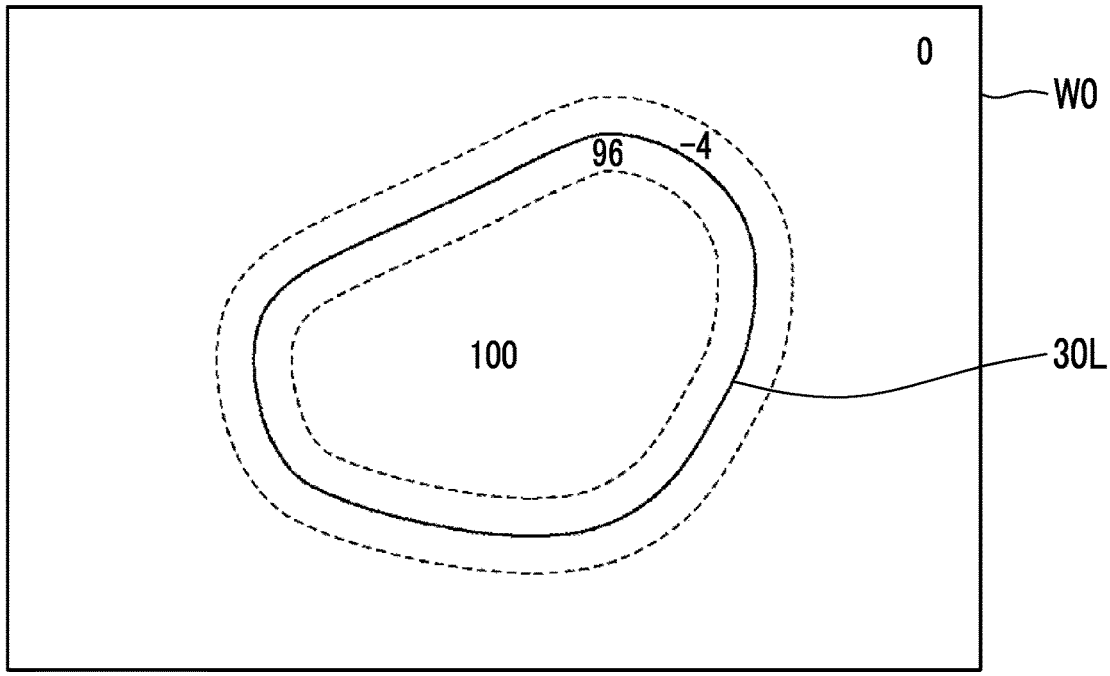
FIG. 9 is a diagram illustrating a weighted image after the weight coefficient is corrected.

Further, in the weighted image W0 illustrated in FIG. 7, in a case where correction for deleting the region A11 is performed as illustrated in FIG. 6, a corrected weight coefficient of −4 is set for the region through which the cursor 40 passes. That is, the corrected weight coefficient of −4 is set for a portion through which the cursor 40 passes inside the boundary 30L of the region of interest 30, and thus the weight coefficient of the portion is 96. Further, the corrected weight coefficient of −4 is set for a portion through which the cursor 40 passes outside the boundary 30L of the region of interest 30, and thus the weight coefficient of the portion is −4. Thereby, the weight coefficients in the weighted image W0 are as illustrated in FIG. 9.

Figure 10:
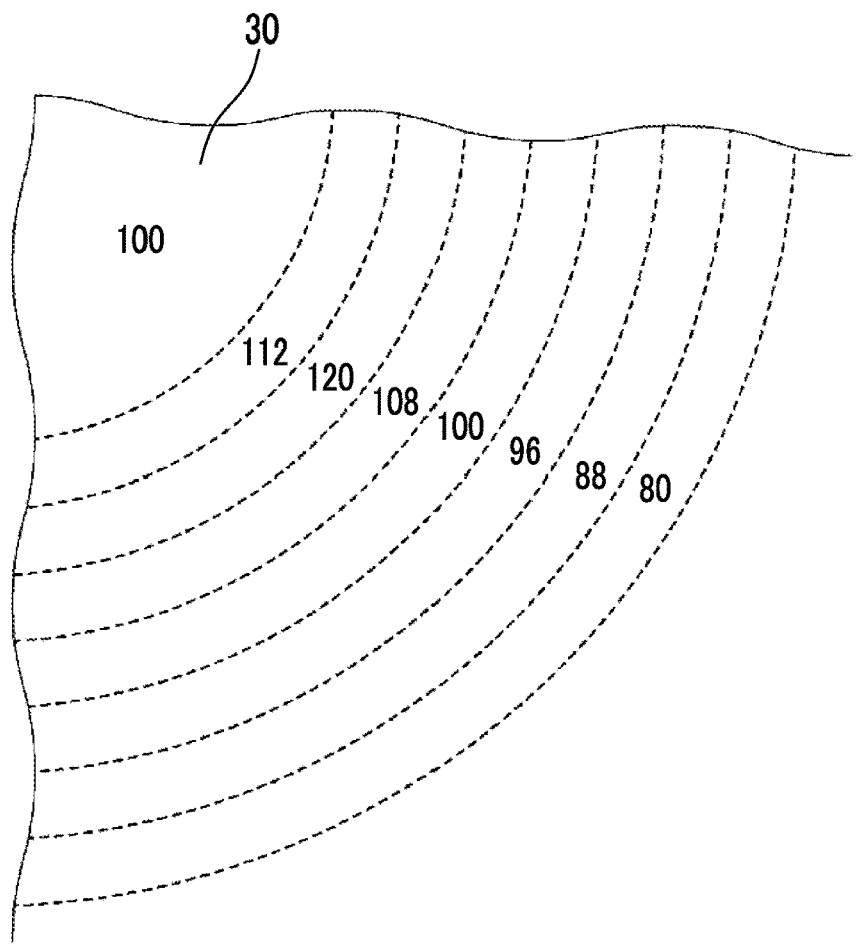
FIG. 10 is a diagram for explaining distribution of weight coefficient values near the boundary of the region of interest.

Here, in the tomographic image Dk, in a case where the boundary of the region of interest 30 as an extraction target is unclear, the intended boundary of the region of interest 30 may differ depending on the user who performs the correction. In addition, even for the same user, the boundary of the region of interest 30 may be changed depending on an editing timing. Further, during a work of correcting the boundary, a threshold value of the image for defining the boundary may be changed. In such a case, in order to improve learning accuracy of a determiner included in the region of interest extraction unit 22, it is necessary to acquire more accurate learning data by correcting the boundary of the region of interest 30. For this reason, in a case where the boundary of the region of interest 30 extracted from the tomographic image is unclear, the user repeats editing such as adding or deleting the region to or from the boundary of the region of interest 30, and thus the boundary of the region of interest 30 is determined. Thereby, in the weighted image W0, as illustrated in FIG. 10, values of the weight coefficients are distributed in contour lines near the boundary of the region of interest.

The threshold value setting unit 26 sets a threshold value for extracting the region of interest in the weighted image W0. Specifically, the threshold value may be set by the input from the input unit 15 by the user.

In the weighted image W0, the corresponding region extraction unit 27 sets, as the boundary of the region of interest 30, a boundary of a region of which a threshold value is equal to or larger than the threshold value which is set by the threshold value setting unit 26, and extracts, from the tomographic image Dk (or three-dimensional image G0) from which the weighted image W0 is generated, as the corresponding region, a region corresponding to the region including pixels of which the weight coefficient is equal to or larger than the threshold value in the weighted image W0. For example, in a case where the weight coefficients in the weighted image W0 are as illustrated in FIG. 10 and the threshold value is set to 100, a boundary between the region of which the weight coefficient is 100 and the region of which the weight coefficient is 96 is set as the boundary of the region of interest, and the corresponding region is extracted from the tomographic image Dk (or three-dimensional image G0).

Figure 11:
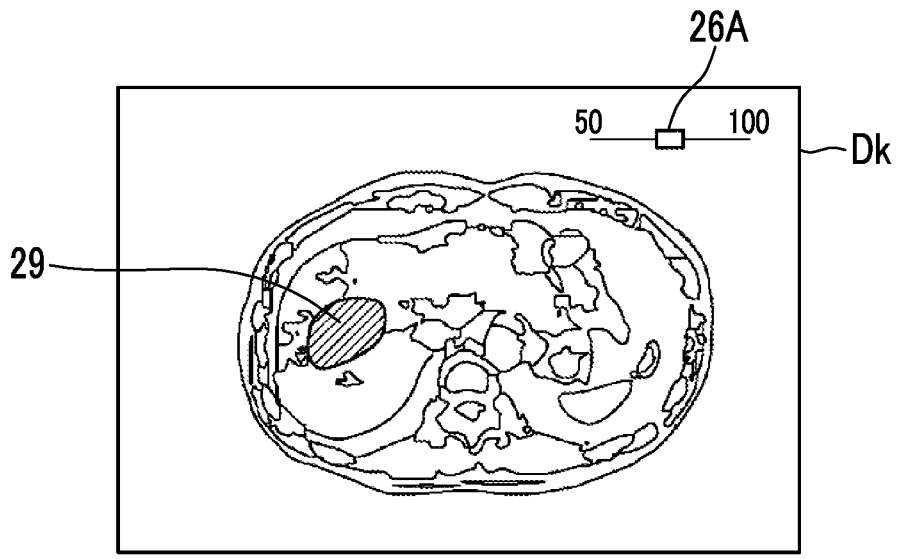
FIG. 11 is a diagram illustrating a state where a slider is displayed in a tomographic image from which a corresponding region is extracted.

The corresponding region extracted by the corresponding region extraction unit 27 may be displayed on the display unit 14, and the user who views the displayed corresponding region may input change of the threshold value. In this case, as illustrated in FIG. 11, a slider 26A may be displayed on the display unit 14, and the user may input change of the threshold value via an instruction from the input unit 15 to slide the slider 26A. Here, in the slider 26A illustrated in FIG. 11, the threshold value may be set between 50 and 100. In this case, in a case where the threshold value is changed by the slider 26A, a size of the extracted corresponding region 29 is changed according to the set threshold value. That is, as the threshold value becomes smaller, the size of the extracted corresponding region 29 becomes larger, and as the threshold value becomes larger, the size of the extracted corresponding region 29 becomes smaller.

The corresponding region extraction unit 27 associates the weighted image W0 generated by the image generation unit 25 with the corresponding region and stores the weighted image W0 associated with the corresponding region in the storage 13. Alternatively, the weighted image W0 is stored in an external storage apparatus such as an image storage server 3 via the network 4. Since the weighted image W0 is generated for each of the tomographic images Dj included in the three-dimensional image G0, the stored weighted image W0 is a three-dimensional image. Further, similar to the weighted image W0, the corresponding region is also a three-dimensional image.

Figure 12:
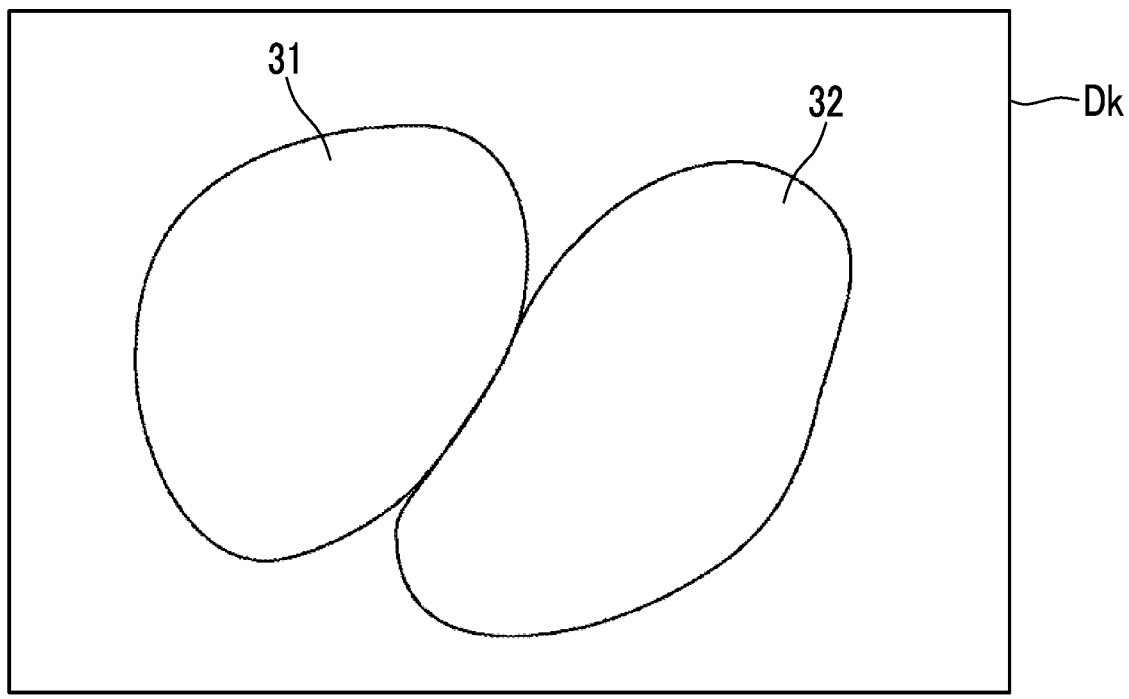
FIG. 12 is a diagram illustrating a state where an extracted first region of interest and an extracted second region of interest are adjacent to each other.
Figure 13:
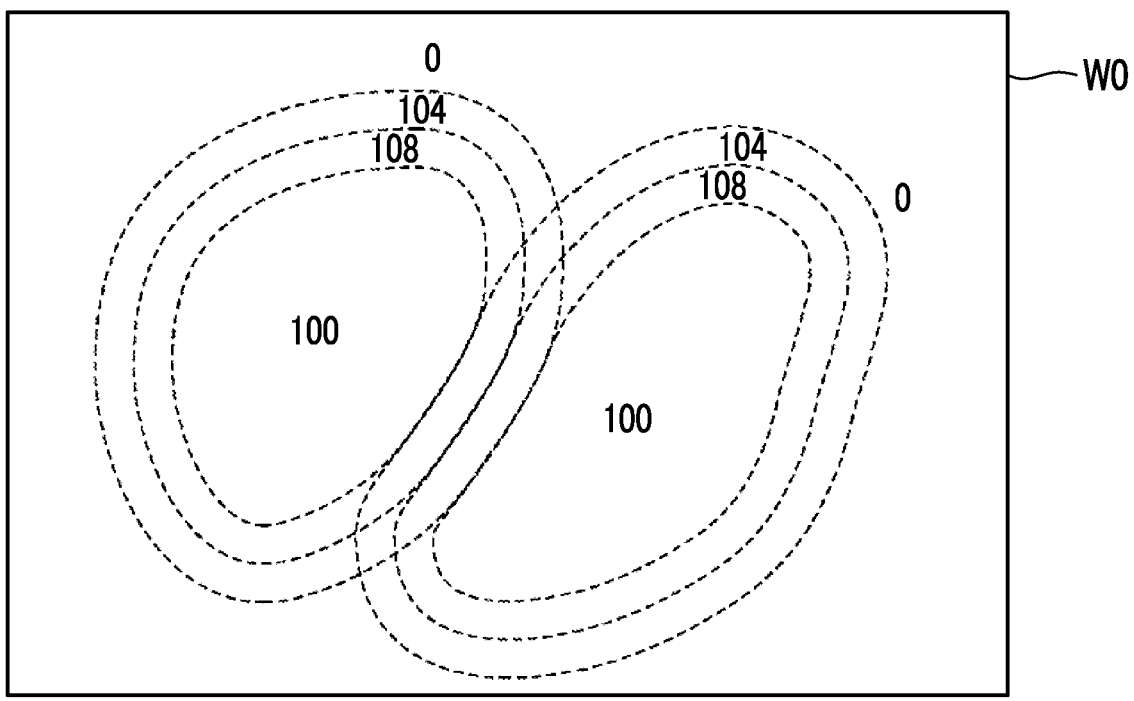
FIG. 13 is a diagram illustrating a weighted image in which weight coefficients are set for each of the first region of interest and the second region of interest.

A plurality of regions of interest may be extracted from the tomographic image Dk. In a case where a plurality of regions of interest are extracted in this way, the region of interests may be adjacent to each other. In such a case, a correction instruction for each of the plurality of adjacent regions of interest may be performed. For example, as illustrated in FIG. 12, in a case where a first region of interest 31 and a second region of interest 32 are adjacent to each other, the correction unit 24 separately performs a correction for each of the first region of interest 31 and the second region of interest 32. Thereby, the image generation unit 25 sets a first weight coefficient for the first region of interest 31 and sets a second weight coefficient for the second region of interest 32 in the weighted image W0. FIG. 13 is a diagram illustrating a weighted image in which weight coefficients are set for each of the first region of interest 31 and the second region of interest.

Figure 14:
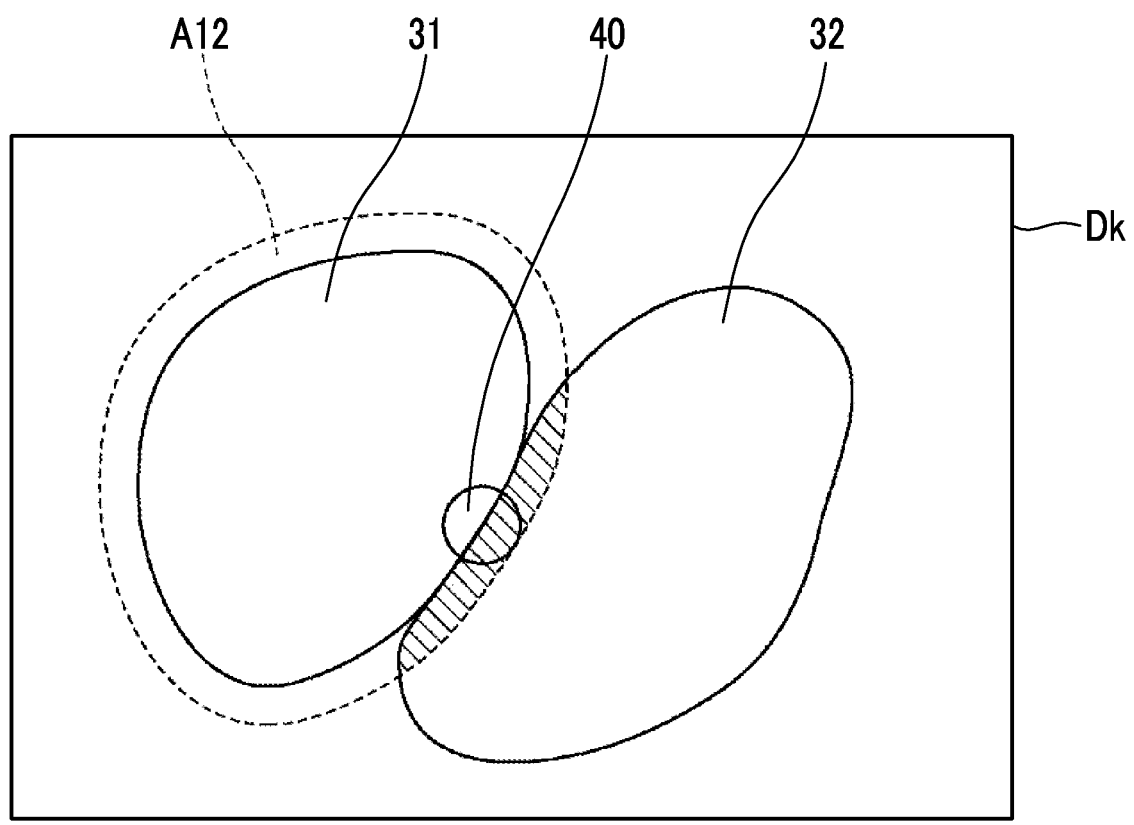
FIG. 14 is a diagram for explaining correction of the weight coefficients using a cursor in a case where the first region of interest and the second region of interest are adjacent to each other.
Figure 15:
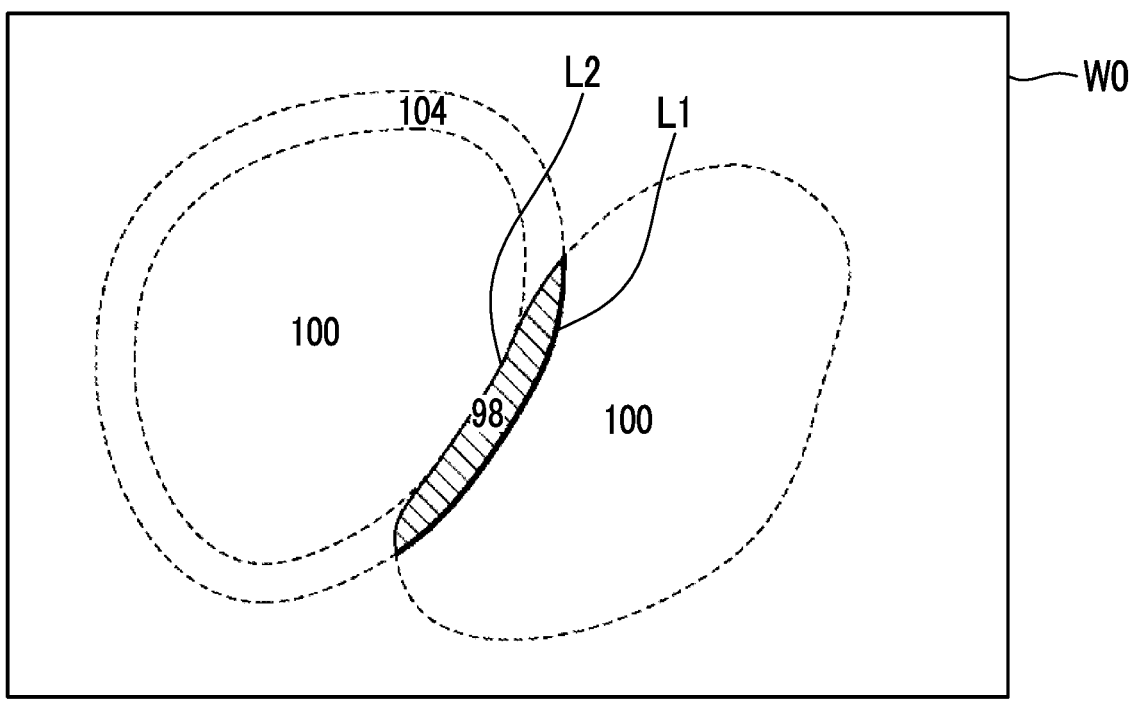
FIG. 15 is a diagram for explaining correction of the weight coefficients in a case where the first region of interest and the second region of interest are adjacent to each other.

On the other hand, in a portion at which the first region of interest 31 and the second region of interest 32 are adjacent to each other, correction of the boundary of one of the first region of interest 31 and the second region of interest 32 may be applied to correction of the boundary of the other of the first region of interest 31 and the second region of interest 32. For example, as illustrated in FIG. 14, in a case where the region A12 is added to the first region of interest 31 by using the cursor 40, for the first region of interest 31, the weight coefficient of the region A12 is set to 104. On the other hand, in the portion at which the first region of interest 31 and the second region of interest 32 are adjacent to each other, for the second region of interest 32, the weight coefficient of the region through which the cursor 40 passes (indicated by a broken line in FIG. 14) is set to, for example, −2. Thereby, in the weighted image W0 illustrated in FIG. 15, for the first region of interest 31, the weight coefficient near a center of a region corresponding to the first region of interest 31 is set to 100, and the weight coefficient outside the region is set to 104. On the other hand, for the second region of interest 32, the weight coefficient near a center of a region corresponding to the second region of interest 32 is set to 100, and the weight coefficient of the region through which the cursor 40 passes, which is indicated by a diagonal line, is set to 98. In FIG. 15, in a portion at which the first region of interest 31 and the second region of interest 32 are in contact with each other, only the weight coefficient "98" of the second region of interest 32 is illustrated.

In a case where the weighted image W0 is generated in this way, the boundary between the first region of interest 31 and the second region of interest 32 is different according to the threshold value for extracting the region of interest. That is, assuming that the threshold value of the boundary with the second region of interest 32 is set to 100, the boundary at the portion at which the first region of interest 31 and the second region of interest 32 are adjacent to each other is indicated by a line L1. Further, assuming that the threshold value of the boundary with the second region of interest 32 is set to 98, the boundary at the portion at which the first region of interest 31 and the second region of interest 32 are in contact with each other is indicated by a line L2.

Figure 16:
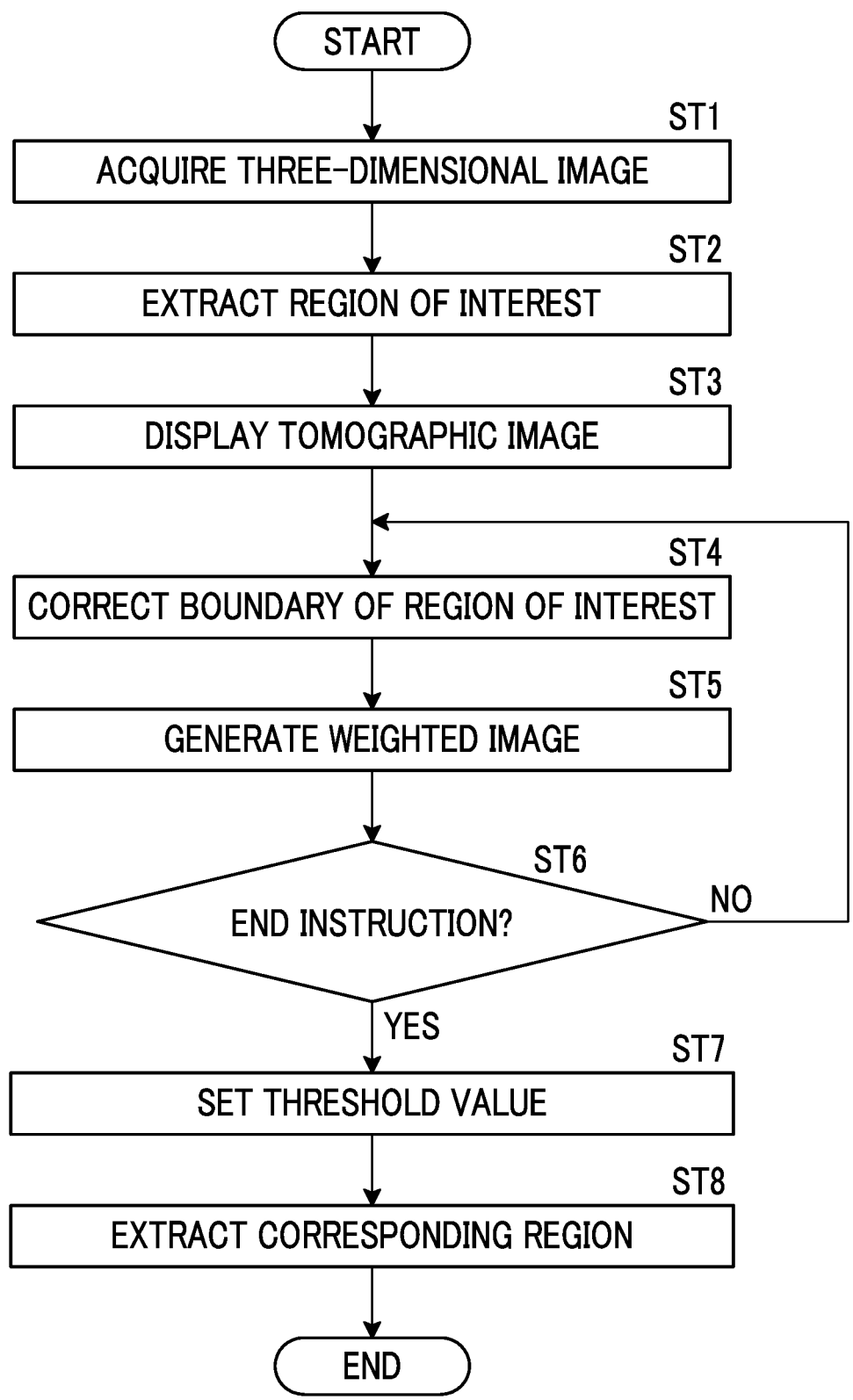
FIG. 16 is a flowchart illustrating weighted image generation processing performed in the present embodiment.

Next, weighted image generation processing performed in the present embodiment will be described. FIG. 16 is a flowchart illustrating weighted image generation processing performed in the present embodiment. First, the image acquisition unit 21 acquires a three-dimensional image G0 (step ST1). Next, the region of interest extraction unit 22 extracts a region of interest from the three-dimensional image G0 (step ST2). The display control unit 23 displays one tomographic image Dk among the plurality of tomographic images Dj included in the three-dimensional image G0, on the display unit 14 (step ST3).

The correction unit 24 corrects a boundary 30L of the extracted region of interest 30 in the tomographic image Dk according to a correction instruction for the boundary 30L of the extracted region of interest 30 using the input unit 15 by the user (step ST4). The image generation unit 25 generates a weighted image according to the correction instruction by the correction unit 24 (step ST5). It is determined whether or not a correction end instruction is performed (step ST6). In a case where a determination result in step ST6 is NO, the process returns to step ST4. In a case where a determination result in step ST6 is YES, the threshold value setting unit 26 sets a threshold value for the weight coefficient according to an instruction by the user (step ST7). The corresponding region extraction unit 27 extracts, from the tomographic image Dk, a corresponding region corresponding to a region including pixels of which the weight coefficient is equal to or larger than the threshold value in the weighted image W0 (step ST8), and the process is ended.

As described above, in the present embodiment, the three-dimensional image G0, that is, the tomographic image Dk is displayed on the display unit 14, and a correction instruction for the boundary of the region of interest in the displayed tomographic image Dk is received. In addition, an initial weight coefficient is set for the extracted region of interest, and a corrected weight coefficient is set for the corrected region for which the correction instruction is given in the tomographic image Dk. Thus, a weighted image W0 is generated in which each pixel in the tomographic image Dk has, as a pixel value of each pixel, the weight coefficient representing a weight of being within the region of interest. In the weighted image W0 generated in this way, the region of interest has a pixel value according to the correction instruction. Thus, the certainty that the region of interest is in the weighted image W0 can be recognized according to the pixel value of the weighted image W0. Therefore, according to the present disclosure, by reflecting the correction of the boundary by referring to the weighted image W0, it is possible to set the region of interest in the tomographic image Dk, and further, in the three-dimensional image G0.

In the above embodiment, the tomographic images Dk included in the three-dimensional image G0 are sequentially displayed, and correction of the region of interest and generation of the weighted image are performed. On the other hand, the three-dimensional image G0 may be displayed on the display unit 14 by, for example, projection using a well-known projection method, and correction of the region of interest and generation of the weighted image W0 may be performed on the displayed three-dimensional image G0.

Figure 17:
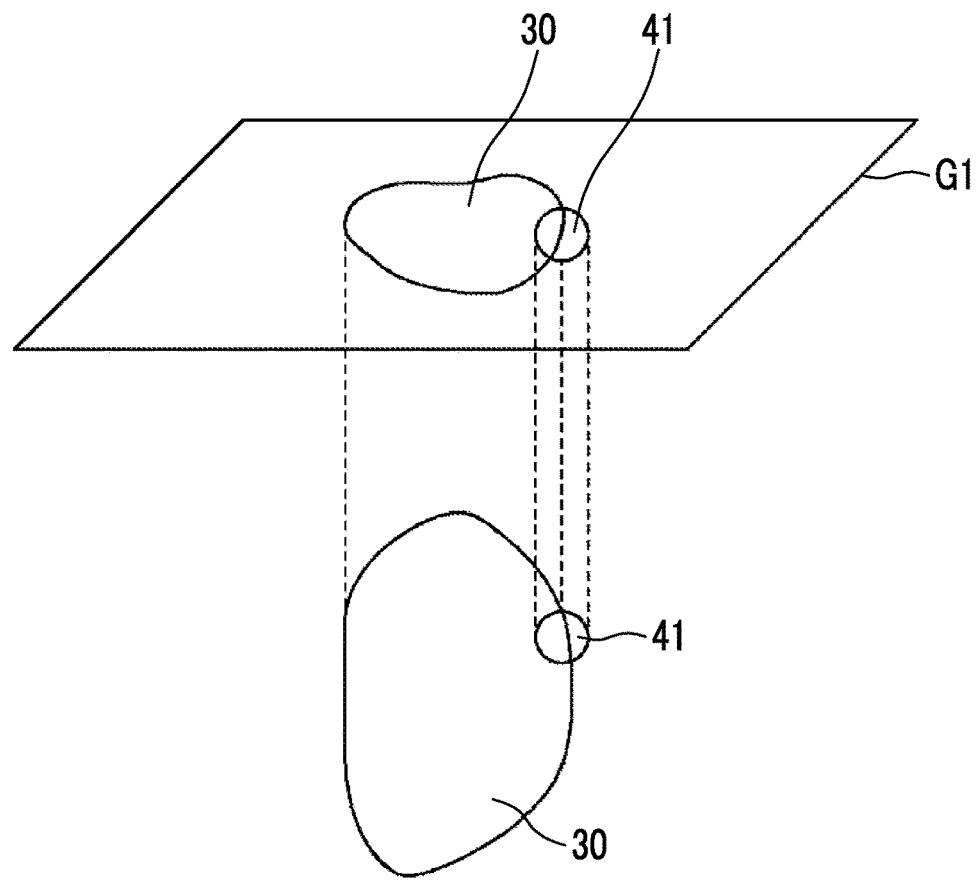
FIG. 17 is a diagram for explaining correction of a boundary in a three-dimensional image.

FIG. 17 is a diagram for explaining correction of the boundary in the three-dimensional image G0. As illustrated in FIG. 17, a projected image G1 of the three-dimensional image G0 is obtained by two-dimensionally projecting the region of interest 30 having a three-dimensional shape. The user corrects the boundary on the displayed projected image G1 using a cursor 41 having a spherical shape. On the other hand, since the two-dimensional projected image G1 is actually displayed on the display unit 14, the cursor 41 looks like a circular shape on the projected image G1. Therefore, the user corrects the boundary of the region of interest 30 in the projected image G1 using the cursor 41 which looks like a circular shape.

Figure 18:
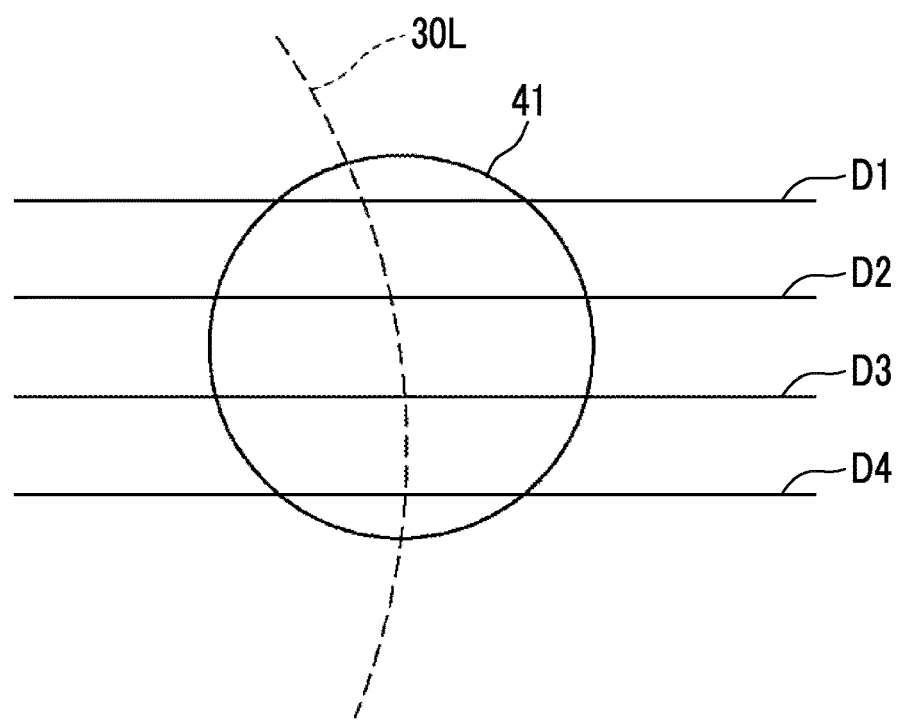
FIG. 18 is a diagram illustrating tomographic images in a cursor having a spherical shape.
Figure 19:
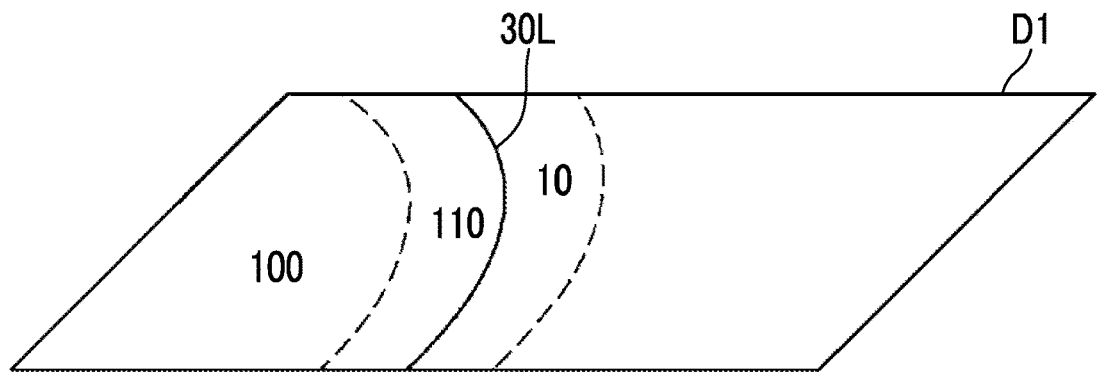
FIG. 19 is a diagram for explaining a difference in weight coefficients in a case of correcting the weight coefficients in a three-dimensional image.
Figure 19:
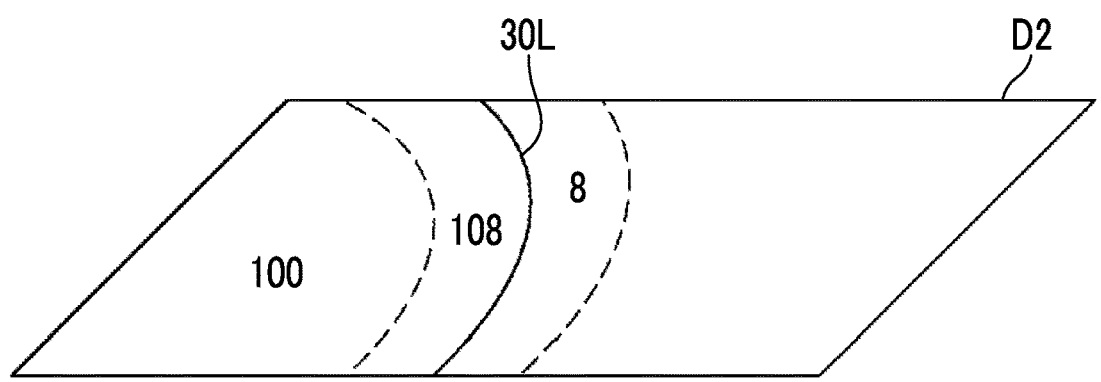
Figure 19:
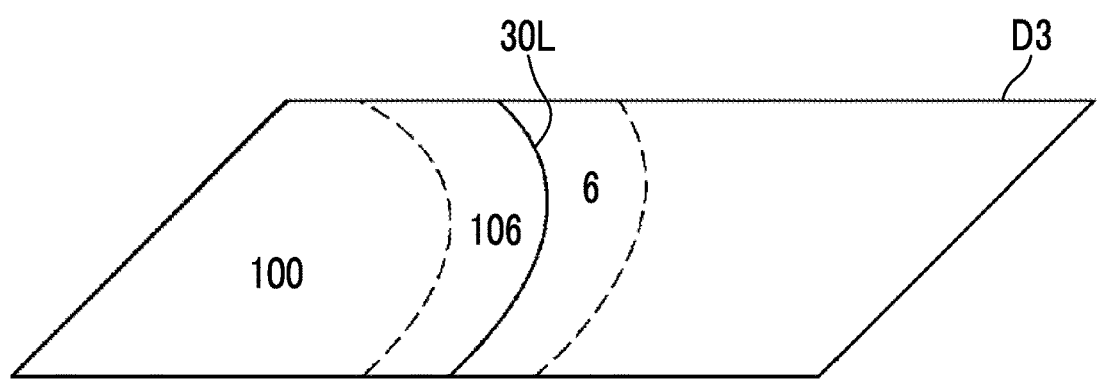
Figure 19:
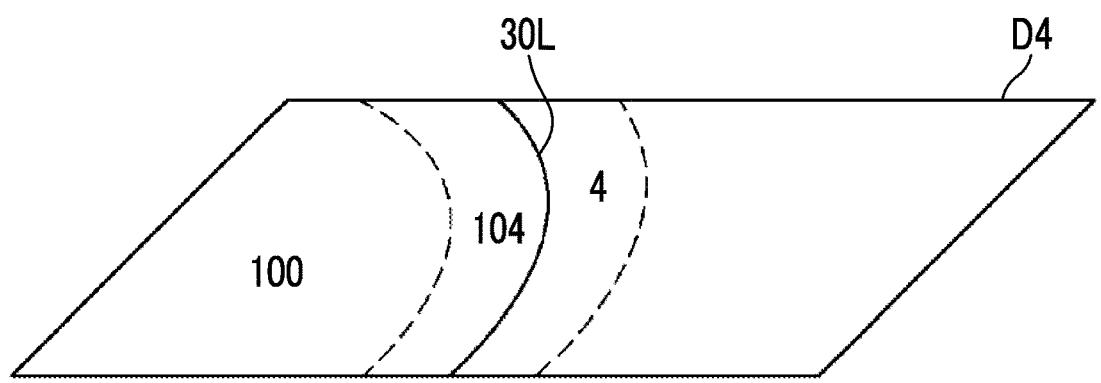

In a case where correction of the boundary is performed in this way, as illustrated in FIG. 18, a plurality of tomographic images (here, four) D1 to D4 are included in the three-dimensional image G0 in a depth direction of the cursor 41 having a spherical shape. In this case, in the displayed projected image G1, the weight coefficient for a pixel which can be visually recognized may be set to be larger than the weight coefficient for a pixel which cannot be visually recognized. For example, as illustrated in FIG. 19, in the tomographic image D1 that can be visually recognized in the projected image G1, the corrected weight coefficient of the added region may be set to +10. In the tomographic images D2 to D4 that cannot be visually recognized in the projected image G1, as a distance from the tomographic image D1 increases, the corrected weight coefficients may be reduced in order of +8, +6, and +4.

Further, in the above embodiment, the corrected weight coefficients may be set to different values according to the type of the region of interest. For example, there are dozens of types of lung-related diseases, and the dozens of types of diseases can be classified into a small classification, a middle classification, and a large classification. In this case, correction for the large classification has a greater effect on classification of the region of interest as compared with correction for the small classification. Therefore, preferably, the corrected weight coefficient for the large classification is set to be larger than the corrected weight coefficient for the small classification.

Figure 20:
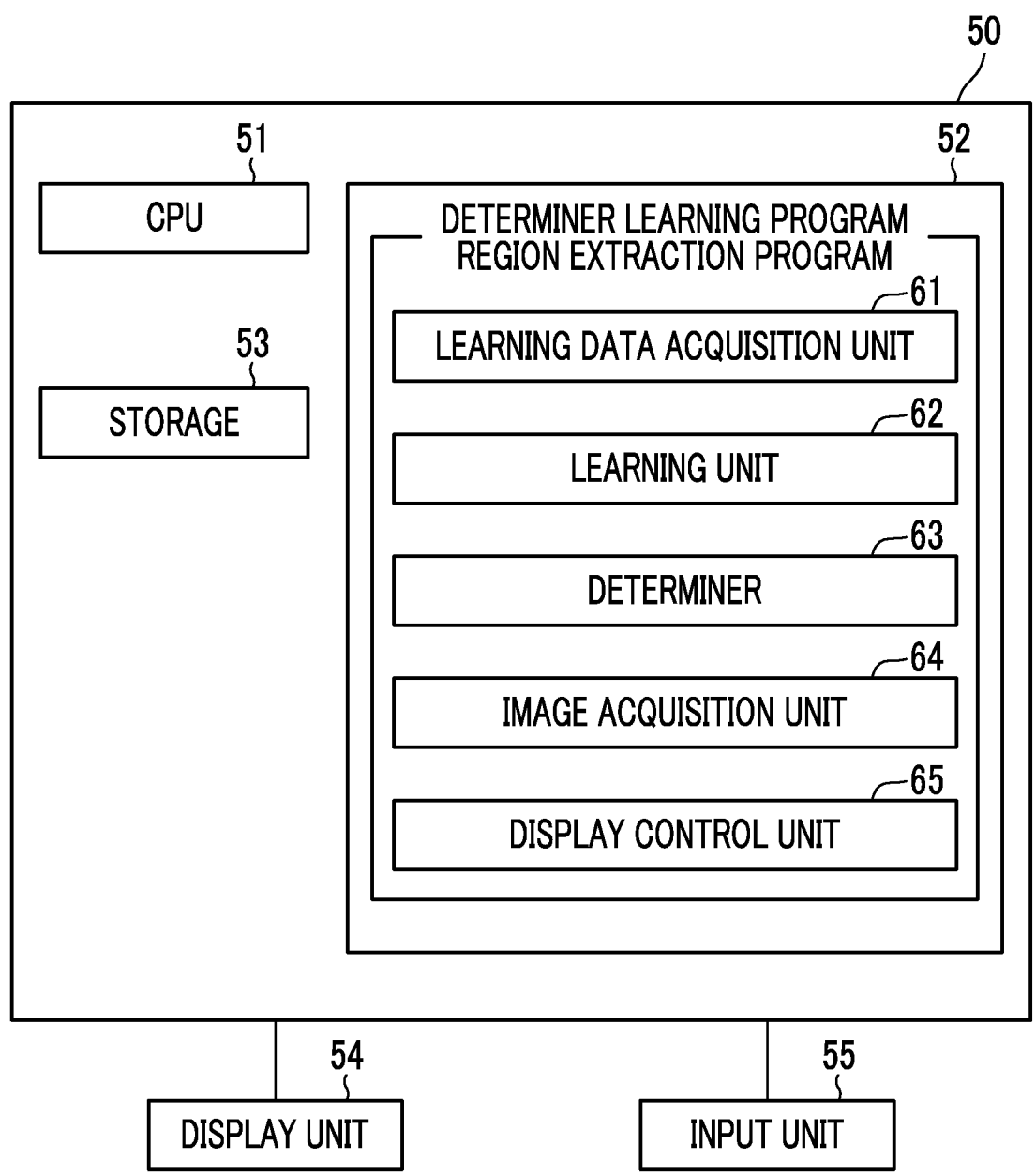
FIG. 20 is a diagram illustrating a schematic configuration of a region extraction apparatus including a determiner learning apparatus according to the embodiment of the present disclosure.

Next, embodiments of a determiner learning apparatus, a determiner, and a region extraction apparatus according to the present disclosure will be described. FIG. 20 is a diagram illustrating a schematic configuration of a region extraction apparatus including a determiner learning apparatus that is realized by installing a determiner learning program and a region extraction program in a computer. As illustrated in FIG. 20, a region extraction apparatus 50 includes a CPU 51, a memory 52, and a storage 53 as a standard workstation configuration. Further, a display unit 54 such as a liquid crystal display and an input unit 55 such as a keyboard and a mouse are connected to the region extraction apparatus 50.

The determiner learning program and the region extraction program are stored in the memory 52. The determiner learning program defines, as processing to be executed by the CPU 51, learning data acquisition processing of acquiring, as learning data, the weighted image W0 generated by the weighted image generation apparatus 1 according to the present embodiment and an image of the corresponding region extracted from the weighted image W0, and learning processing of learning, using a plurality of pieces of learning data, a determiner that outputs a determination result of the region of interest included in the three-dimensional image G0 in a case where the three-dimensional image G0 is input. Further, the region extraction program defines, as processing to be executed by the CPU 51, image acquisition processing of acquiring the three-dimensional image G0 including the region of interest as a determination target, and display control processing of displaying a determination result of the region of interest by the determiner.

In a case where the CPU 51 executes pieces of processing according to the program, the computer functions as a learning data acquisition unit 61, a learning unit 62, a determiner 63, an image acquisition unit 64, and a display control unit 65.

The learning data acquisition unit 61 acquires, as learning data, the weighted image W0 generated by the weighted image generation apparatus 1 and the image of the corresponding region extracted from the three-dimensional image G0, from the image storage server 3. In a case where the learning data is already stored in the storage 53, the learning data acquisition unit 61 may acquire the learning data from the storage 53.

In a case where the three-dimensional image G0 is input, the learning unit 62 learns the determiner 63 for determining the region of interest in the three-dimensional image G0 using a plurality of pieces of learning data. In the present embodiment, in a case where the three-dimensional image G0 including the region of interest as an extraction target is input, the determiner 63 outputs a determination result of the region of interest included in the three-dimensional image G0. Specifically, the determiner 63 determines whether each voxel of the three-dimensional image G0 as a determination target is within the region of interest or within a region other than the region of interest, and outputs the determination result. Thus, the learning unit 62 performs learning of the determiner 63, that is, machine learning by acquiring feature data in a region having a predetermined size (for example, 3×3 or the like) from a plurality of pieces of learning data (that is, the weighted image W0 and the image of the corresponding region) and inputting the acquired feature data to the determiner 63 such that a determination result of the region of interest is output. The determination result is a numerical value representing a certainty that each pixel included in the three-dimensional image G0 is within the region of interest, for example, as a percentage. Further, the learning is performed by a predetermined number of times or until a determination result of the region of interest reaches a predetermined certainty (for example, 99%).

The learning is performed in this way, thereby generating the determiner 63 that determines, in a case where a three-dimensional image G0 is input, a region of interest in the three-dimensional image G0 by classifying voxels of the three-dimensional image G0 into the region of interest and a region other than the region of interest.

As the determiner 63, a support vector machine, a deep neural network, a convolutional neural network, a recurrent neural network, or the like may be used.

The image acquisition unit 64 acquires, from the image storage server 3, the three-dimensional image G0 including the region of interest as an extraction target. In a case where the three-dimensional image G0 is already stored in the storage 53, the image acquisition unit 64 may acquire the three-dimensional image G0 from the storage 53.

Figure 21:
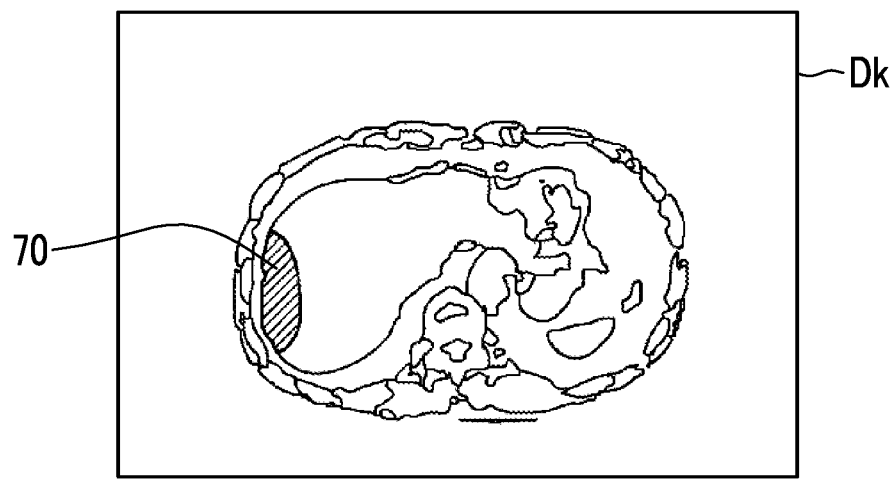
FIG. 21 is a diagram illustrating a determination result of the region of interest.

The display control unit 65 displays, on the display unit 54, the determination result of the region of interest by the determiner 63. Specifically, the determined region of interest is highlighted in the three-dimensional image G0. FIG. 21 is a diagram illustrating a determination result of the region of interest. As illustrated in FIG. 21, in one tomographic image Dk of the three-dimensional images G0, hatching is added to the determined region of interest 70, and thus the region of interest 70 is highlighted. Instead of adding hatching, the region of interest 70 may be highlighted by surrounding the region of interest 70 with a contour line, or the region of interest 70 may be highlighted by masking a region other than the region of interest 70.

Figure 22:
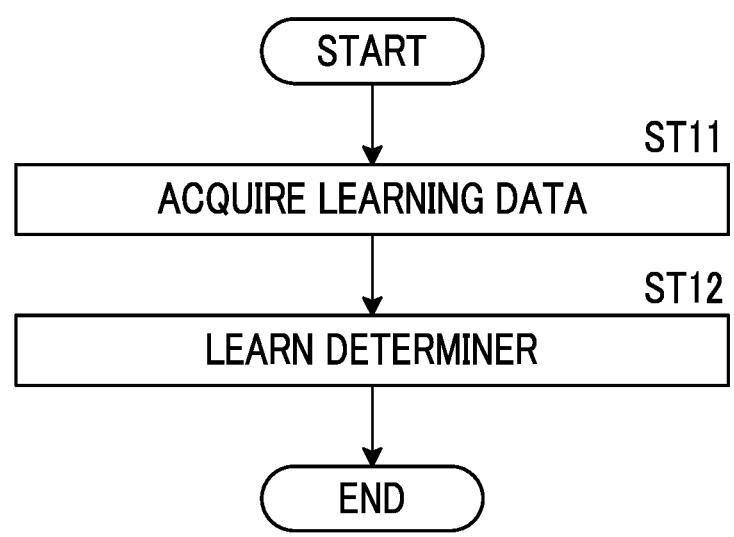
FIG. 22 is a flowchart illustrating learning processing performed in the present embodiment.

Next, learning processing according to the present embodiment will be described. FIG. 22 is a flowchart illustrating learning processing performed in the present embodiment. First, the learning data acquisition unit 61 acquires learning data (step ST11). Next, in a case where a three-dimensional image G0 is input, the learning unit 62 learns the determiner 63 that determines a region of interest in the three-dimensional image G0 using a plurality of pieces of learning data (step ST12), and the process is ended.

Figure 23:
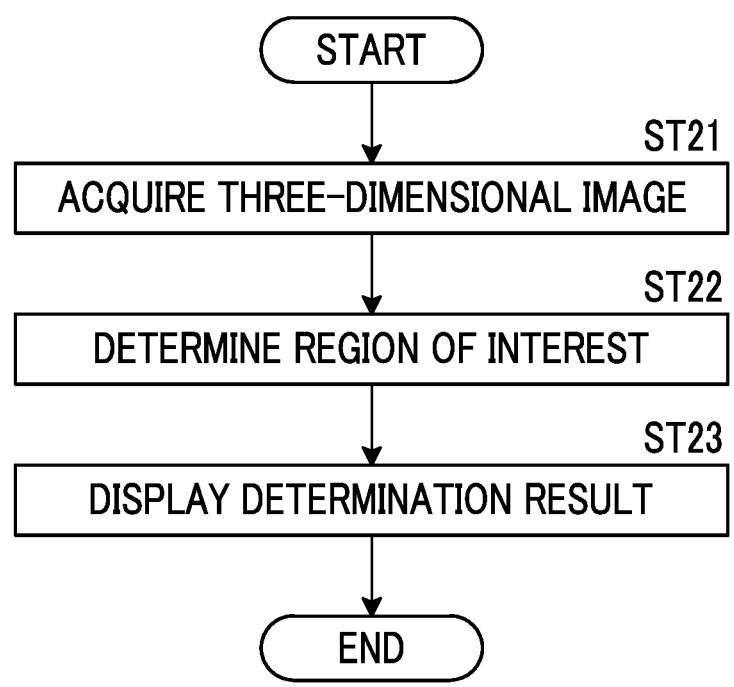
FIG. 23 is a flowchart illustrating region determination processing performed in the present embodiment.

Next, region determination processing according to the present embodiment will be described. FIG. 23 is a flowchart of region determination processing according to the present embodiment. First, the image acquisition unit 64 acquires a three-dimensional image G0 including a region of interest as a determination target (step ST21). The determiner 63 determines the region of interest in the three-dimensional image G0 (step ST22). Next, the display control unit 65 displays a determination result of the region of interest by the determiner 63 (step ST23), and the process is ended.

In the above embodiment, the weighted image generation apparatus includes the region of interest extraction unit 22. On the other hand, the present disclosure is not limited thereto. The region of interest may be extracted by a separate apparatus connected to the weighted image generation apparatus via the network 4. Further, the acquired three-dimensional image G0 may include a region of interest already extracted.

Further, in the above embodiment, for example, as a hardware structure of a processing unit that executes various processing such as processing performed by the image acquisition unit 21, the region of interest extraction unit 22, the display control unit 23, the correction unit 24, the image generation unit 25, the threshold value setting unit 26, the corresponding region extraction unit 27, the learning data acquisition unit 61, the learning unit 62, the determiner 63, the image acquisition unit 64, and the display control unit 65, the following various processors may be used. The various processors include, as described above, a CPU, which is a general-purpose processor that functions as various processing units by executing software (a program), and a dedicated electric circuit, which is a processor having a circuit configuration specifically designed to execute a specific processing, such as a programmable logic device (PLD) or an application specific integrated circuit (ASIC) that is a processor of which the circuit configuration may be changed after manufacturing such as a field programmable gate array (FPGA).

One processing unit may be configured by one of these various processors, or may be configured by a combination of two or more processors having the same type or different types (for example, a combination of a plurality of FPGAs or a combination of a CPU and an FPGA). Further, the plurality of processing units may be configured by one processor.

As an example in which the plurality of processing units are configured by one processor, firstly, as represented by a computer such as a client and a server, a form in which one processor is configured by a combination of one or more CPUs and software and the processor functions as the plurality of processing units may be adopted. Secondly, as represented by a system on chip (SoC) or the like, a form may be adopted in which a processor that realizes the function of the entire system including the plurality of processing units by one integrated circuit (IC) chip is used.

As described above, the various processing units are configured by using one or more various processors as a hardware structure.

Further, as the hardware structure of the various processors, more specifically, an electric circuit (circuitry) in which circuit elements such as semiconductor elements are combined may be used.

What is claimed is:

1. A weighted image generation apparatus comprising at least one processor, wherein the processor is configured to:
   display a medical image from which at least one region of interest is extracted on a display;
   correct a boundary of the region of interest according to a correction instruction for the extracted region of interest; and
   generate a weighted image in which each pixel in the medical image has, as a pixel value of each pixel, a weight coefficient representing a certainty of being within the region of interest, by setting an initial weight coefficient for the extracted region of interest and setting a corrected weight coefficient for a corrected region based on the correction instruction in the medical image.

2. The weighted image generation apparatus according to claim 1,
   wherein the processor is configured to set at least one of corrected weight coefficients having different values according to content of the correction instruction.

3. The weighted image generation apparatus according to claim 2,
   wherein the processor is configured to set a corrected weight coefficient having a positive value for the corrected region in a case where the correction instruction is a region addition instruction, and set a corrected weight coefficient having a negative value for the corrected region in a case where the correction instruction is a region deletion instruction.

4. The weighted image generation apparatus according to claim 1,
   wherein, in a case where a plurality of regions of interest are extracted from the medical image,
   the processor is configured to correct a boundary of each of the plurality of regions of interest according to the correction instruction for each of the plurality of regions of interest, and
   set the weight coefficients for each of the plurality of regions of interest.

5. The weighted image generation apparatus according to claim 4,
   wherein, in a case where the plurality of regions of interest are adjacent to each other, the processor is configured to set boundaries of the plurality of regions of interest in the weighted image according to the weight coefficients which are set for each of the plurality of regions of interest.

6. The weighted image generation apparatus according to claim 4,
   wherein the processor is configured to set, according to the correction instruction for one region of interest among the plurality of regions of interest, the corrected weight coefficients for other regions of interest other than the one region of interest.

7. The weighted image generation apparatus according to claim 4,
   wherein the processor is configured to set boundaries of the plurality of regions of interest according to a threshold value which is set for the weight coefficient of at least one region of interest among the plurality of regions of interest.

8. The weighted image generation apparatus according to claim 1,
wherein the processor is configured to set at least one of corrected weight coefficients having different values according to a type of the region of interest.

9. The weighted image generation apparatus according to claim 1,
wherein, in a case where the medical image is a three-dimensional image, the processor is configured to set, in the medical image displayed on the display, the corrected weight coefficient for a visually recognizable pixel to be larger than the corrected weight coefficient for a visually unrecognizable pixel.

10. The weighted image generation apparatus according to claim 1, wherein the processor is configured to:
set a threshold value for the weight coefficient; and
extract, from the medical image, a corresponding region corresponding to a region for which the weight coefficient is equal to or larger than the threshold value in the weighted image.

11. A determiner learning apparatus comprising at least one processor, wherein the processor is configured to:
acquire, as learning data, the weighted image generated by the weighted image generation apparatus according to claim 10 and an image of the corresponding region extracted from the medical image; and
learn a determiner, which outputs a determination result of a region of interest included in the medical image in a case where the medical image is input, using a plurality of pieces of the learning data.

12. A determiner learned by the determiner learning apparatus according to claim 11.

13. A region extraction apparatus comprising at least one processor, wherein the processor is configured to:
acquire a medical image including a region of interest as a determination target; and
determine the region of interest in the medical image by the determiner according to claim 12.

14. The region extraction apparatus according to claim 13, wherein the processor is configured to display a determination result of the region of interest by the determiner.

15. A weighted image generation method comprising:
displaying a medical image from which at least one region of interest is extracted on a display;
correcting a boundary of the region of interest according to a correction instruction for the extracted region of interest; and
generating a weighted image in which each pixel in the medical image has, as a pixel value of each pixel, a weight coefficient representing a certainty of being within the region of interest, by setting an initial weight coefficient for the extracted region of interest and setting a corrected weight coefficient for a corrected region based on the correction instruction in the medical image.

16. A determiner learning method comprising:
acquiring, as learning data, the weighted image generated by the weighted image generation method according to claim 15 and an image of a corresponding region extracted from the medical image and corresponding to a region for which the weight coefficient is equal to or larger than a threshold value in the weighted image; and
learning a determiner, which outputs a determination result of a region of interest included in the medical image in a case where the medical image is input, using a plurality of pieces of the learning data.

17. A region extraction method comprising:
acquiring a medical image including a region of interest as a determination target; and
determining the region of interest in the medical image by the determiner according to claim 12.

18. A non-transitory computer-readable storage medium that stores a weighted image generation program causing a computer to execute:
displaying a medical image from which at least one region of interest is extracted on a display;
correcting a boundary of the region of interest according to a correction instruction for the extracted region of interest; and
generating a weighted image in which each pixel in the medical image has, as a pixel value of each pixel, a weight coefficient representing a certainty of being within the region of interest, by setting an initial weight coefficient for the extracted region of interest and setting a corrected weight coefficient for a corrected region based on the correction instruction in the medical image.

19. A non-transitory computer-readable storage medium that stores a determiner learning program causing a computer to execute:
acquiring, as learning data, the weighted image generated by the weighted image generation method according to claim 15 and an image of a corresponding region extracted from the medical image and corresponding to a region for which the weight coefficient is equal to or larger than a threshold value in the weighted image; and
learning a determiner, which outputs a determination result of a region of interest included in the medical image in a case where the medical image is input, using a plurality of pieces of the learning data.

20. A non-transitory computer-readable storage medium that stores a region extraction program causing a computer to execute:
acquiring a medical image including a region of interest as a determination target; and
determining the region of interest in the medical image via the determiner according to claim 12.

* * * * *